(12) United States Patent
Abdel-Rahman

(10) Patent No.: US 10,238,317 B2
(45) Date of Patent: Mar. 26, 2019

(54) MUAC Z-SCORE TAPE AND METHODS OF USE THEREOF

(71) Applicant: The Children's Mercy Hospital, Kansas City, MO (US)

(72) Inventor: Susan M. Abdel-Rahman, Kansas City, MO (US)

(73) Assignee: The Children's Mercy Hospital, Kansas City, MO (US)

(*) Notice: Subject to any disclaimer, the term of this patent is extended or adjusted under 35 U.S.C. 154(b) by 226 days.

(21) Appl. No.: 15/149,829

(22) Filed: May 9, 2016

(65) Prior Publication Data

US 2016/0324444 A1    Nov. 10, 2016

Related U.S. Application Data

(60) Provisional application No. 62/158,421, filed on May 7, 2015.

(51) Int. Cl.
| | | |
|---|---|---|
| *A41H 1/02* | (2006.01) | |
| *A61B 5/00* | (2006.01) | |
| *G01B 3/10* | (2006.01) | |
| *G01B 5/02* | (2006.01) | |
| *A61B 5/107* | (2006.01) | |

(52) U.S. Cl.
CPC .......... *A61B 5/1075* (2013.01); *A61B 5/4866* (2013.01); *A61B 5/6823* (2013.01); *A41H 1/02* (2013.01); *A61B 5/1072* (2013.01); *A61B 5/6824* (2013.01); *A61B 2503/04* (2013.01); *A61B 2503/045* (2013.01); *A61B 2503/06* (2013.01); *G01B 3/1082* (2013.01); *G01B 5/025* (2013.01)

(58) Field of Classification Search
CPC ..... A61B 5/107; A61B 5/1072; A61B 5/1075; A61B 5/4866; A61B 5/6823; A61B 5/6824; A61B 2503/04; A61B 2503/045; A61B 2503/06; A41H 1/02; G01B 3/1082; G01B 5/025
See application file for complete search history.

(56) References Cited

U.S. PATENT DOCUMENTS

| | | | | |
|---|---|---|---|---|
| 2008/0183421 A1* | 7/2008 | Chai | ...................... | A61B 5/107 702/173 |
| 2013/0267872 A1* | 10/2013 | Bhangoo | .............. | A61B 5/1072 600/587 |

OTHER PUBLICATIONS

Fenton et al., "Using the LMS method to calculate z-score for the Fenton preterm infant growth chart", European Journal of Clinical Nutrition, vol. 61, Feb. 14, 2007, pp. 1380-1385.*

* cited by examiner

*Primary Examiner* — Devin B Henson
(74) *Attorney, Agent, or Firm* — Hovey Williams LLP

(57) ABSTRACT

The present disclosure is directed towards a device, method of using a device, and a method of making a device for predicting the nutritional status in an individual of any age or weight. The device includes one or more strips for measuring the circumference of a body part of an individual. The method includes taking the girth measurement and reading a standard score from the device to estimate the nutritional status of the individual.

19 Claims, 7 Drawing Sheets
(6 of 7 Drawing Sheet(s) Filed in Color)

Figure 2:
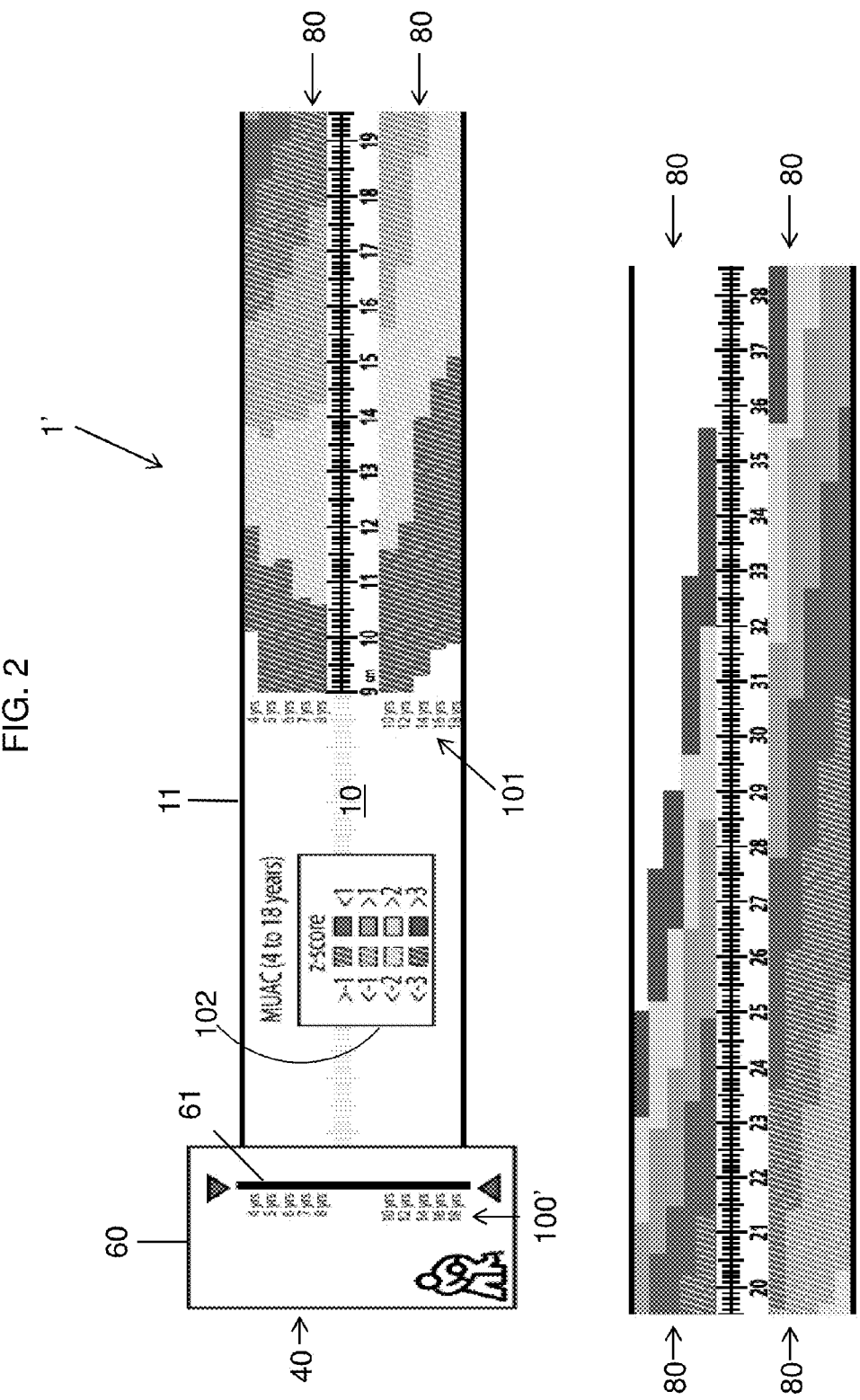

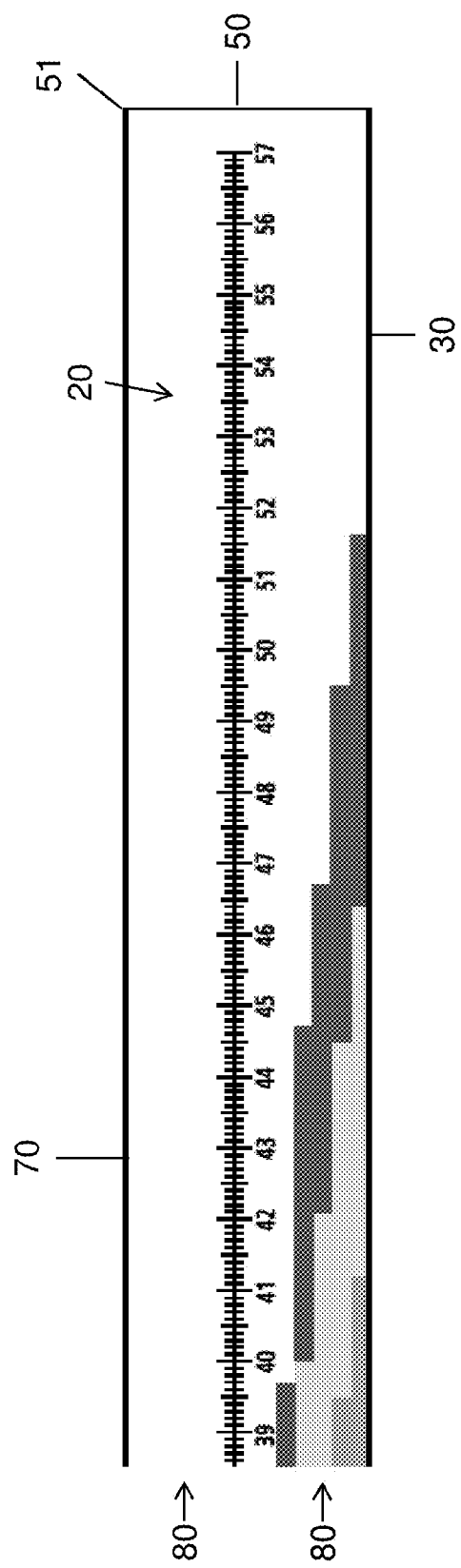
FIG. 2 Con't

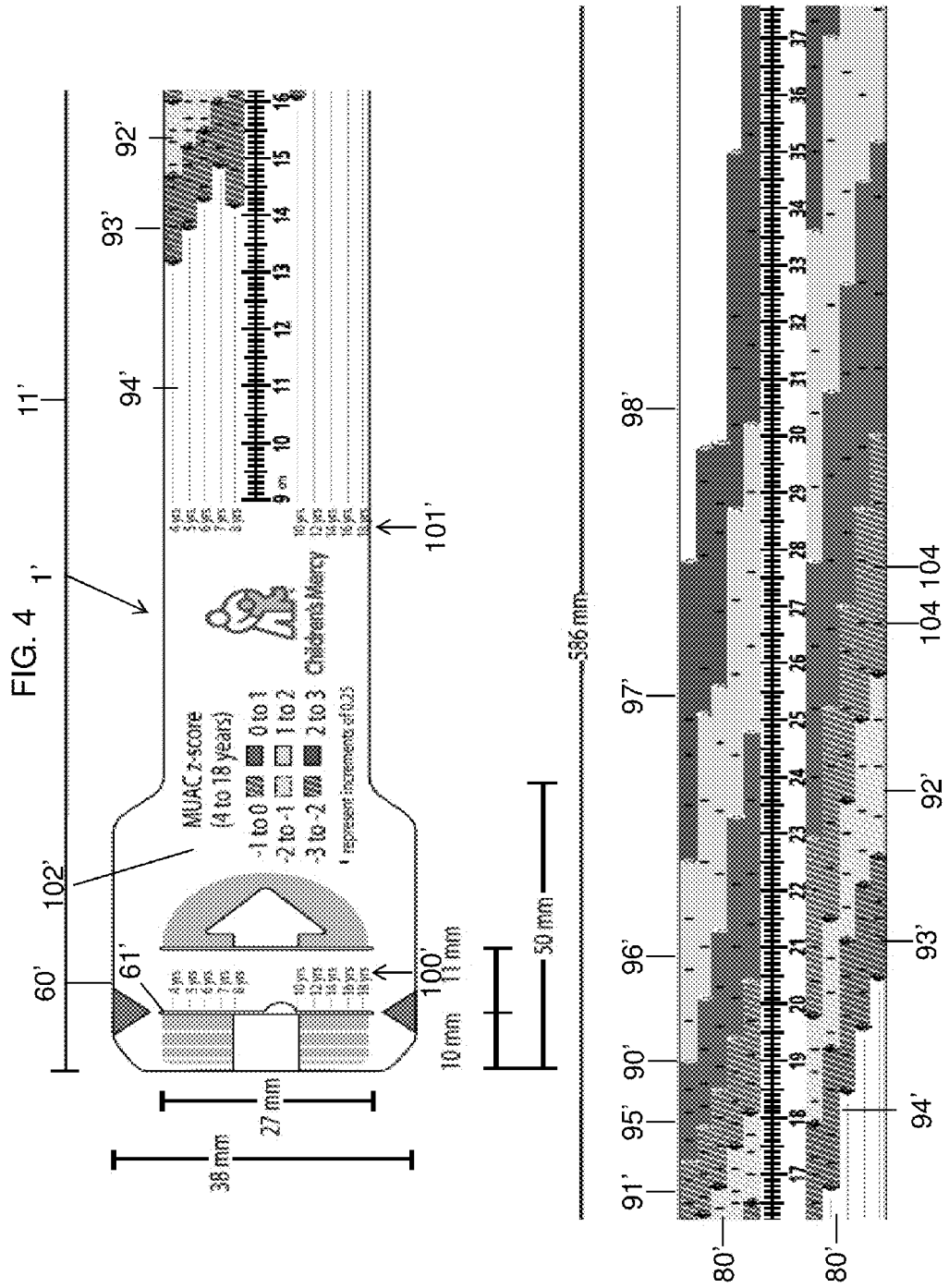

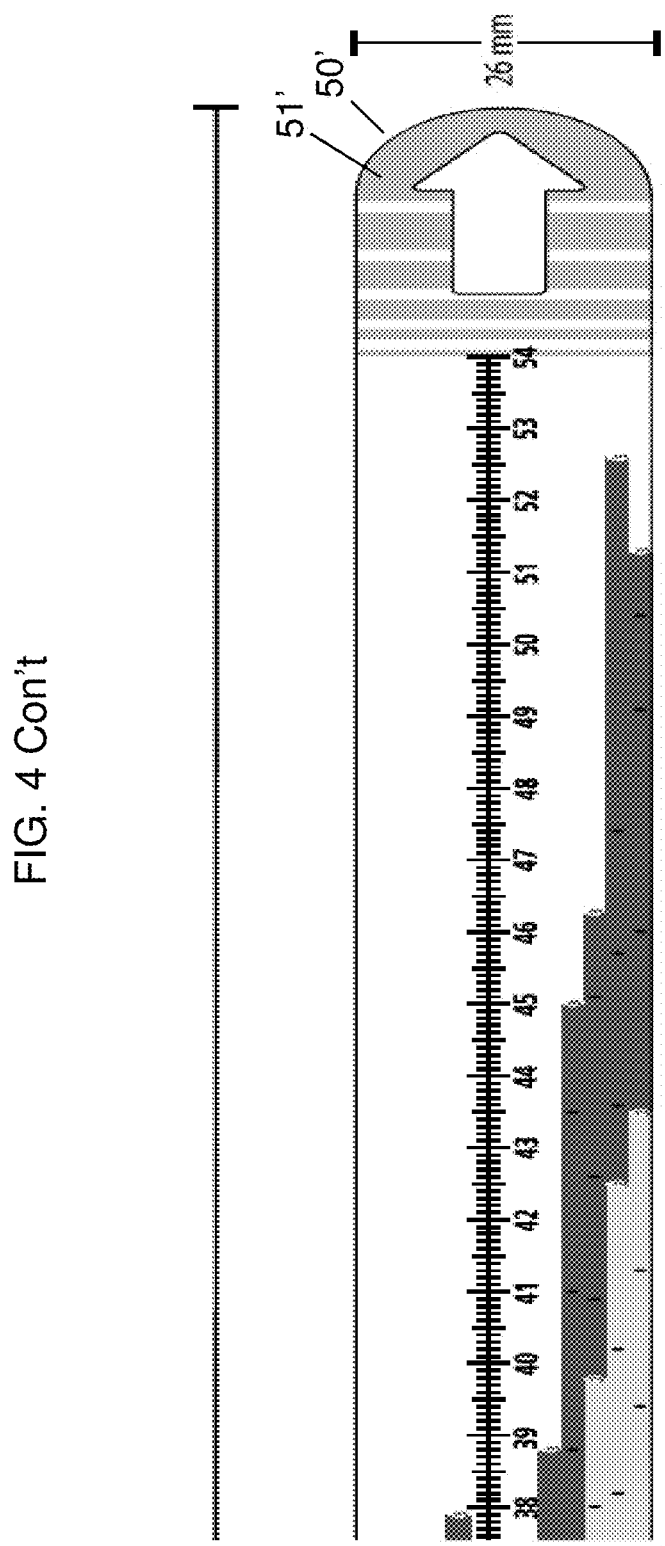
FIG. 4 Con't

MUAC Z-SCORE TAPE AND METHODS OF USE THEREOF

BACKGROUND

The World Health Organization has determined that anthropometry, the comparative measurement and study of the human body, reflects both nutritional and health status and that it is predictive of performance, health, survival, and the risk of disease. Anthropometric measurements can also be used to assess the need of an individual for special services such as nutritional rehabilitation and support, or to assess the response of a patient to an intervention. The middle-upper arm circumference (MUAC) of an individual is an anthropometric measurement known to be a reliable indicator of skeletal protein and subcutaneous fat, both important determinants of malnutrition. In some studies, MUAC has been found to be better at predicting death in children than any other anthropometric indicator. The MUAC measurement, which is taken on the left arm, at the mid-point between the tip of the shoulder (i.e., the upper edge of the posterior border of the acromion process) and the tip of the elbow (i.e., the olecranon process), has been widely adopted as a favored anthropometric technique. MUAC measurement has been vigorously promoted as the preferred anthropometric technique by the World Health Organization (WHO), United Nations Children's Fund (UNICEF), and many governmental and private health organizations throughout the world. In addition to its value as a nutritional status assessment tool, MUAC measurement is favored because it requires no expensive equipment or extensive training, is portable, easy to use and widely applicable. MUAC measurement can be taken regardless of the age or health status of the individual or the ability to stand, sit or walk. MUAC measurements can be taken on even the most debilitated individuals.

Currently MUAC is widely used by international agencies to evaluate the nutritional status of children in medically underserved areas such as developing nations. More recently, The Academy of Nutrition and Dietetics and the American Society for Parenteral and Enteral Nutrition drafted a consensus statement with recommendations for diagnosing and documenting pediatric malnutrition in the United States, (Becker et al. J Acad. Nutr. Diet. 2014; 114: 1988-2000). MUAC was among the indicators of malnutrition the consensus panel recommended for evaluation. The panel proposed that "MUAC measurements should be part of the full anthropometric assessment in all patients, and are particularly important in those whose weight may be affected by lower-extremity edema, ascites, or steroids, as weight trends alone are unreliable related to fluid status. When serial z scores are unavailable, serial MUAC measurements can be used to monitor changes in body composition using the child as his or her own control. MUAC has been indicated as a more sensitive prognostic indicator for mortality than weight-for-height parameters in malnourished pediatric patients." These entities advise that, "trained individuals consistently perform these measurements for best long-term comparison of data." They further explicitly recommend that "z score, decline in z score, and negative z score" be used to classify and document pediatric malnutrition.

The World Health Organization has developed Child Growth Standards, comprising a set of population norms for malnutrition based on MUAC measurements for boys and girls from age 3 months to 5 years. While MUAC measurements can be taken with any measuring tape marked in millimeters, nutritional status is determined by referencing a set of norms that establish the measurements associated with various stages of malnutrition. Typically, these norms reflect a standard reference value that represents the central tendency (i.e., the mean or median) arm measurement for a nutritionally healthy child of a given age in the reference population. Variance from the reference mean value is measured in standard deviations. How far (i.e. how many standard deviations) away a child's measurement is from this population mean is represented by a number or standard score commonly known as the z-score. Thus, the reference mean value is assigned a z-score of 0. The various stages of malnutrition (specifically under nutrition) are defined by negative standard deviations from the mean, or negative z-scores. However, the World Health Organization (WHO) has developed a single child growth threshold for the identification of severe acute malnutrition in infants and children that is not based on z-score. It has issued the MUAC measuring tape that incorporates color bands which discriminate between severe acute malnutrition, moderate acute malnutrition, at risk for acute malnutrition, and normal in children up to 5 years of age. Importantly, the WHO MUAC tape reflects singular categorical color-banding thresholds for all children irrespective of age, such that reliability suffers considerably at the extremes of age.

While the use of z-scores in association with MUAC measurements has proven more reliable than the use of percentile deviations from a reference value, MUAC measurements for a population rarely produce a normal distribution represented by a bell-shaped curve. This is particularly true where there are instances of extreme differences in individual measurements within the population. For example, in some populations, the dataset of MUAC population values is skewed, or distributed asymmetrically, resulting in a curve that is shifted to the right or left of the reference value. Though skewness will influence z-scores, this is not accounted for if the MUAC data from the reference population are presumed to fit a normal standard distribution. Additionally, the peak of the distribution curve for the MUAC measurements in a reference population may be taller, sharper, or flatter than a standard bell curve. This so-called excess kurtosis occurs where more of the variability in the measurements is due to a few extreme differences from the reference value, rather than numerous modest differences. On the resulting curve, the probability of intermediate values is less likely and the central and extreme values are more likely. In settings of skewness or excessive kurtosis, the data must first be transformed to generate a near-normal distribution, then curve fit to define the mathematical function that best fits the data (traditionally a cubic spline), and finally back-transformed to arrive at the specific (i.e., lambda, mu, and sigma ("LMS")) values from which the z-score can be calculated.

Currently available MUAC tapes endorsed by the WHO provide MUAC in millimeters and offer a single color scheme to indicate the risk for malnutrition. However, these tapes apply the same threshold values to all children irrespective of age. As discussed above, this singular threshold loses accuracy as children age. Consequently, application of the currently available MUAC tapes does not facilitate longitudinal assessments of children. Further, the currently available MUAC tapes provide no frame of reference for the distance from the mean that these children fall relative to children their own age. Additionally, the existing MUAC tapes do not take into consideration children over the age of 5 years, adolescents, and adults whose nutritional status may also be at risk. Finally, the existing MUAC tapes do not address malnutrition that contributes to overweight and obesity (overnutrition). Such individuals typically do not exhibit the loss of upper arm muscle mass associated with malnourishment and so are overlooked by current MUAC screening devices and methods. However, protein-calorie malnutrition is known to contribute to obesity, and such individuals may require nutrition support to address malnutrition. The current MUAC device does not provide a means to categorize such overweight and obese individuals according to their nutritional status and risk for malnutrition.

What is needed in the art is an improved device and method for estimating the nutritional status of an individual at any age, including an infant, child, adolescent, or adult without regard to variability in the dataset for the reference population. Further, what is needed is such an improved device and method that can be used in a population of all ages and across a broad weight range. Further, what is needed is such an improved device and method that can determine nutritional status (as defined by z-score) in a single step, without the need to identify the correct reference chart and determine a range from the chart. Further, what is needed is a method of making such a device based on creating a scale of numbers, indicia, or symbols that correspond to the circumference of the middle upper arm, middle upper thigh, chest or other circumference and its standard score for individuals of various ages and weights.

SUMMARY OF THE INVENTION

The present disclosure overcomes the problems inherent in the prior art and provides devices and methods for easily estimating the nutritional status of an individual who may be an infant, child, adolescent or adult, and who may be of low or normal weight, overweight, or obese. Additionally, a method for designing such a device for estimating nutritional status is disclosed.

The device and method of the present disclosure incorporate the measurement of circumference as a surrogate for body habitus ("physique") into a nutritional estimation strategy that performs robustly independently of age, weight, gender, and geographic origin over a large range of variables, whether varying independently or together. The present disclosure was developed on the premise that nutritional status for all age, weight, and population groups can be accurately assessed by use of measurements of the circumference of a body part's z-score. The body part can be selected from the middle upper arm, middle thigh, chest, or abdomen. The present disclosure advantageously simplifies the measurement process so that a single measurement of a body part can be made and the z-score range for the nutritional indicator for a particular age and gender within a given population can be simultaneously read directly from the device (as opposed to consulting one or more separate tables or charts to see how the measurement translates into a standard score indicating deviations from the mean).

The device can be designed to reflect z-score ranges calculated from lambda, mu, and sigma (LMS) values that derive from population data that has been transformed and smoothed as described above. Alternatively, the demarcated ranges can reflect the centiles for the raw untransformed data that correspond to selected z-scores as defined in standard normal probability tables. A reference to z-score ranges in this application considers either process.

Preferably, the device consists of one or more strips, each containing a scale of indicia for use in measuring the circumference of a body part of an individual, each strip also containing a scale of indicia showing the standard scores indicating standard deviations above and below the nutritional norm that are associated with the measurement indicia. In one embodiment, the device consists of indicia for obtaining a numerical measurement of the middle-upper arm circumference as well as a plurality of rows or bands of indicia showing standard scores indicating the norm as well as standard deviations above and below the nutritional norm associated with the measurement indicia for designated ages or age ranges. The numerical measurement indicia are arranged in side-by-side correspondence with the age-specific standard score bands. In one embodiment, the indicia indicating the standard deviations also include demarcations that indicate the quarter z-scores, e.g., 0, 0.25, 0.5, 0.75, 1, etc. In another embodiment, the indicia indicating the standard deviations also include demarcations indicating the tenth z-scores, e.g., 0, 0.1, 0.2, 0.3, etc. In another embodiment, the indicia indicating the standard deviations also include demarcations indicating the hundredth z-scores, e.g., 0, 0.01, 0.02, 0.03, etc. It is foreseen that the indicia indicating the standard deviations may also include indicia that indicate the centiles that correspond to a specified standard deviation range. Preferably the strips include numerical indicia designating the age or age range associated with the respective bands of scales of standard scores. Preferably the strips are constructed so that they include an indicator or cursor for indicating the circumference measurement and corresponding standard score. Preferably the indicia showing the scale of standard scores are colored so that a standard score for one age or age range is the same color as the same standard score for another age or age range. It can be appreciated that the indicia showing standard scores will be different depending on the age and population group for which the strip is designed. In one embodiment the device consists of a plurality of strips, each including indicia for measurement and display of standard scores for a particular gender, age, ages, or age range and population. In other embodiments, the circumference of another body part will be used. Preferred body parts include the middle thigh, abdomen, and chest.

The one or more strips that are part of the device can be made from any flexible material that is able to be imprinted and used in measuring the circumference of the middle-upper arm of an individual. Preferably, the strips will also be non-deformable such that any scale of indicia printed thereon will not be deformed (i.e., it will not be distorted) during use, shipping, or storage of the strips. Preferably, the material for the strips can be selected from, but is not limited to, ribbon, plastic compositions, waxed paper, plastic-coated paper, laminated paper, paper, metal, silicon, natural and man-made fibers, and the like. In a most preferred embodiment the one or more strips are made of commonly available fibers, such as paper laminated with a plastic coating.

Preferably, scales of indicia are printed on the strip to indicate linear measurement and standard scores indicating standard deviations from the nutritional norm. The printing can be on either one or both sides of the strip. The indicia can include numbers, letters, symbols, colors, or other indicia. In one preferred embodiment, numbers are printed with a single device corresponding with the linear measurement scale. The circumference of the body part can be shown in any scale of measurement such as inches or centimeters, but preferably is shown in centimeters and millimeters. In the preferred embodiment, color bands are printed on the strip corresponding with the scales of standard scores. The scales of standard scores are aligned with the linear measurement scale to indicate how many standard deviations from normal nutritional status are indicated by a given corresponding linear measurement.

In an embodiment where the device comprises multiple strips, it is sometimes preferred that both sides of the strips are imprinted with indicia to reduce the number of strips required. In one embodiment, the device consists of one or more strips with the measurement scale indicia and corresponding standard score scale indicia for one gender printed on one side, and the measurement scale indicia standard score scale indicia for the other gender printed on the opposite side. In another embodiment, the device consists of strips with the measurement scale indicia and standard score scale indicia for one group of ages or age ranges on one side, and the measurement scale indicia standard score scale indicia for another group of ages or age ranges on the opposite side. In still another embodiment, the device consists of strips with measurement scale indicia and standard score indicia for one population group on one side and measurement scale indicia and standard score scale indicia for another population group on the opposite side. In still another embodiment, the standard score scale indicia reflect data from a designated age or age range in a specific population. As can be appreciated, the device can be arranged in a multitude of different ways depending on the population being measured.

In one embodiment the strips include a measurement portion and a fastener portion. Preferably the fastener portion is located at one end of the tape. Preferably the fastener portion includes an indicator for use in reading the numerical measurement scale and corresponding standard score scale indicia. Preferably the fastener portion includes a slot for receiving the free end of the tape and serving as an indicator. Preferably the fastener portion includes indicia indicating age or age ranges associated with the bands of standard score scale of indicia. Where the standard score scale indicia are color-coded, the tape preferably includes a color key for indicating the standard deviation associated with the corresponding standard score scale indicia. Where the standard score scale indicia are color-coded, the tape may also include a color key for indicating a numerical score or z-score associated with each of the standard score scale indicia.

In one alternate embodiment, an electronic measurement device is employed having measurement means for obtaining a body part circumference measurement, such as a tape, cord, laser or any other suitable means. Additional components of the electronic measurement device that are in wired or wireless communication with the measurement means include various hardware components, such as a processing unit, data storage or system memory including a computer readable medium storing computer executable instructions for executing a program that measures the circumference of the body part and provides a user interface for entering selected parameters regarding the individual to be measured. Such parameters may include one or more of age, gender, demographic information, and any other information relevant to determination of the z-score. Additional hardware components may also include a visual display device, which may include alpha numeric, color, sound or video capability for display of the z-score.

A method for determining the nutritional status of an individual is also disclosed. The method comprises measuring the circumference of a body part of an individual and reading the corresponding standard score from the standard score scale on the tape. Where an electronic measurement device is employed, the method comprises using the user interface to enter selected parameters regarding the individual to be measured, measuring the circumference of a body part of an individual, and reading the z-score from the visual display device. Preferred body parts include the middle upper arm, the middle thigh, the abdomen, and the chest. In a preferred embodiment, the method generally includes the steps of determining the midpoint of the upper arm of an individual and measuring the circumference of the middle-upper arm at the midpoint thereof. In a preferred embodiment, the midpoint of the upper arm is the midpoint between the tip of the shoulder and the tip of the elbow. In another preferred embodiment, the midpoint of the upper arm is the midpoint between the olecranon process and the acromion.

Preferably, the method utilizes a device of the present disclosure. In an embodiment of the method where a device comprising multiple strips is used, each strip is imprinted with a scale of measurement indicia for girth measurement and a plurality of scales of standard score indicia for indicating standard scores associated with nutritional norms for preselected ages or age ranges. The imprinted indicia may also take into account gender, and/or population group. In this embodiment, the method includes measuring the circumference of a body part of a member of the corresponding gender, age and population group by identifying the corresponding measurement scale indicium with the measurement indicator and reading the corresponding standard score from the standard score scale associated with the age of the individual. In an embodiment of the method where the device consists of strips imprinted on both sides, one side of the strip is used for measuring the body part's circumference and reading the corresponding age or age-range specific standard score on one side for a member of the corresponding gender and/or population group, and the other side is used for measuring and reading the score for a member of a different age, gender, or population group. In this embodiment, each of the circumference measurements will correspond to a different scale of indicia on each respective side of the strip. In an embodiment where the device comprises an electronic measurement device, the processing unit executes instructions, such as program modules, with reference to stored data to determine the z-score with reference to z-score ranges calculated as previously described. Preferred body parts include the middle-upper arm, middle thigh, abdomen, and chest.

A method for making the device of the present disclosure is also disclosed. The method includes the steps of obtaining one or more datasets correlating measurements of the body part's circumference with nutritional status at various ages using a mathematical equation to create one or more scales based on the one or more datasets that correlate the circumference measurement to nutritional norms according to age, and printing one or more strips with the scales and standard score indicia to create a device for estimating nutritional status. Preferably, this method results in the device of the present disclosure that is used according to the method of using the device disclosed herein. Where the method involves use of an electronic measurement device, the method includes the steps of obtaining one or more datasets correlating measurements of the body part's circumference with nutritional status at various ages using a mathematical equation to create one or more scales based on the one or more datasets that correlate the circumferential measurement to nutritional norms according to age, providing the scales that correlated the measurements to nutritional norms in the form of computer-readable data accessible to the processing unit, and including such scales in a device that measures the circumference of a body part. Preferred body parts include the middle-upper arm, middle thigh, abdomen, and chest.

In use, electronic devices in accordance with the present disclosure would measure circumference by recording the distance traveled by a ball, roller, laser, or the like, as it was placed on the skin of the body part and moved about the circumference of the body part. In another embodiment of an electronic device, the device includes a measuring tape that can be wrapped about the circumference of the body part to be measured. The measuring tape is then drawn up against the body part by means of a retraction mechanism which can be manual, automated, or even electronically controlled. The measurement is then recorded by conventional means and correlated with the scales in order to determine nutritional status.

The method generally includes obtaining one or more datasets and examining circumference measurements of a body part against the median circumference measurements of nutritionally healthy individuals with the same circumference measurement values. From this, a mathematical model, preferably, a mathematical model with one or more empirically determined parameters or "constants", is developed which predicts nutritional status. Preferred body parts include the middle-upper arm, middle thigh, abdomen, and chest.

The device and methods of the present disclosure are preferably made for infants, children, adolescents, adults, males, and females as well as a wide variety of population groups. Strips designed for members of one or more combinations of these groups would simply use different dataset(s) to determine a different scale of numbers and/or indicia corresponding to circumference measurements. Further, the device and methods of the present disclosure can be customized to fit different populations of adults and children depending on different factors such as, but not limited to, geographic origin, age, ethnic background, and other social factors.

In preferred forms, the present disclosure provides a device for estimating nutritional status of an individual of any age or weight wherein the device generally includes a flexible elongate strip having a front side and a back side. Preferably, each of the front side and the back side includes two scales of indicia thereon. Preferably, a first scale of indicia on the front side provides a first value when the strip is used to measure the circumference of a body part, and a second scale of indicia on the front side provides a nutritional health standard score second value corresponding to the first value. A third scale of indicia on the back side provides a third value when the strip is used to measure the circumference of a body part, and a fourth scale of indicia on the back side provides a nutritional health standard score fourth value corresponding to the third value. The second value may take into account age, gender or a designated population group, and the fourth value may take into account a different age, gender or designated population group. In preferred forms, the first and third scales of indicia for the front side and the back side are in 1 cm and 1 mm gradations or in 1 cm and 0.5 cm and 1 mm gradations. One particularly preferred scale for measuring the circumference or girth of the middle of the upper arm (the midpoint of the humerus) has 1 mm, 0.5 cm, and 1 cm gradations on the scale of indicia from 9.0 cm to 57.0 cm. It is understood that if the scale begins at 9 cm, a small number of individuals will fall outside of the gradations. However, the scale can be started at a lower number, e.g. 8, cm, 7, cm, 6 cm, etc. Additionally, in electronic versions, the scale can begin at any number greater than zero. Preferably, the indicia on each scale of indicia are in a form selected from the group consisting of numbers, letters, symbols, colors, and combinations thereof. One particularly preferred scale of indicia for measuring the standard score corresponding to the scale of indicia for measuring girth has gradations corresponding to standard scores of greater than −1, less than −1, less than −2 and less than −3 and less than 1, greater than 1, greater than 2 and greater than 3. Preferred body parts include the middle-upper arm, middle thigh, abdomen, and chest.

Another preferred device for estimating nutritional status of an individual of any age or weight wherein the device generally includes a plurality of flexible elongate strips, each having a front side and a back side. Preferably, each of the front side and the back side includes two scales of indicia thereon. Preferably, a first scale of indicia on the front side provides a first value when the strip is used to measure the circumference of a body part, and a second scale of indicia on the front side provides a nutritional health standard score second value corresponding to the first value. A third scale of indicia on the back side provides a third value when the strip is used to measure the circumference of the body part, and a fourth scale of indicia on the back side provides a nutritional health standard score fourth value corresponding to the third value. The second value may take into account age, gender or a designated population group, and the fourth value may take into account a different age, gender or designated population group. In preferred forms, the first and third scales of indicia for the front side and the back side are in 1 cm and 1 mm gradations or in 1 cm and 0.5 cm and 1 mm gradations. One particularly preferred scale for measuring the circumference or girth of the middle of the upper arm (the midpoint of the humerus) has 1 mm, 0.5 cm, and 1 cm gradations on the scale of indicia from 9.0 cm to 57.0 cm. Preferably, the indicia on each scale of indicia are in a form selected from the group consisting of numbers, letters, symbols, colors, and combinations thereof. One particularly preferred scale for measuring the standard score corresponding to the scale for measuring girth has gradations corresponding to standard scores of greater than −1, less than −1, less than −2 and less than −3 and less than 1, greater than 1, greater than 2 and greater than 3. Each side of each strip may be customized to fit a different age group, gender or population or combination thereof. Groups of strips may be customized to fit different age and gender groups within a particular population. Preferred body parts include the middle-upper arm, middle thigh, abdomen, and chest.

The present application may be described in the context of computer-executable instructions, such as program modules, being executed by a computer. Generally, program modules include routines, programs, objects, components, data structures, and so forth, which perform particular tasks or implement particular abstract data types.

The present disclosure provides for a suitable computing and networking environment that may be used to implement various aspects of the present disclosure. The computing and networking environment generally includes a general purpose computing device, although it is contemplated that the networking environment may include other computing systems, such as personal computers, server computers, handheld or laptop devices, tablet devices, multiprocessor systems, microprocessor-based systems, set top boxes, programmable consumer electronic devices, network PCs, minicomputers, mainframe computers, digital signal processors, state machines, logic circuitries, distributed computing environments that include any of the above computing systems or devices, and the like.

Components of the computer may include various hardware components, such as a processing unit, a data storage (e.g., a system memory), and a system bus that couples various system components of the computer to the processing unit. The system bus may be any of several types of bus structures including a memory bus or memory controller, a peripheral bus, and a local bus using any of a variety of bus architectures. For example, such architectures may include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

The computer may further include a variety of computer-readable media that includes removable/non-removable media and volatile/nonvolatile media, but excludes transitory propagated signals. Computer-readable media may also include computer storage media and communication media. Computer storage media includes removable/non-removable media and volatile/nonvolatile media implemented in any method or technology for storage of information, such as computer-readable instructions, data structures, program modules or other data, such as RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that may be used to store the desired information/data and which may be accessed by the computer. Communication media includes computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. For example, communication media may include wired media such as a wired network or direct-wired connection and wireless media such as acoustic, RF, infrared, and/or other wireless media, or some combination thereof. Computer-readable media may be embodied as a computer program product, such as software stored on computer storage media.

The data storage or system memory includes computer storage media in the form of volatile/nonvolatile memory such as read only memory (ROM) and random access memory (RAM). A basic input/output system (BIOS), containing the basic routines that help to transfer information between elements within the computer (e.g., during start-up) is typically stored in ROM. RAM typically contains data and/or program modules that are immediately accessible to and/or presently being operated on by processing unit. For example, in one embodiment, data storage holds an operating system, application programs, and other program modules and program data.

Data storage may also include other removable/non-removable, volatile/nonvolatile computer storage media. For example, data storage may be: a hard disk drive that reads from or writes to non-removable, nonvolatile magnetic media; a magnetic disk drive that reads from or writes to a removable, nonvolatile magnetic disk; and/or an optical disk drive that reads from or writes to a removable, nonvolatile optical disk such as a CD-ROM or other optical media. Other removable/non-removable, volatile/nonvolatile computer storage media may include magnetic tape cassettes, flash memory cards, digital versatile disks, digital video tape, solid state RAM, solid state ROM, and the like. The drives and their associated computer storage media, described above provide storage of computer-readable instructions, data structures, program modules and other data for the computer.

A user may enter commands and information through a user interface or other input devices such as a tablet, electronic digitizer, a microphone, keyboard, and/or pointing device, commonly referred to as mouse, trackball or touch pad. Other input devices may include a joystick, game pad, satellite dish, scanner, or the like. Additionally, voice inputs, gesture inputs (e.g., via hands or fingers), or other natural user interfaces may also be used with the appropriate input devices, such as a microphone, camera, tablet, touch pad, glove, or other sensor. These and other input devices are often connected to the processing unit through a user interface that is coupled to the system bus, but may be connected by other interface and bus structures, such as a parallel port, game port or a universal serial bus (USB). A monitor or other type of display device is also connected to the system bus via an interface, such as a video interface. The monitor may also be integrated with a touch-screen panel or the like.

The computer may operate in a networked or cloud-computing environment using logical connections of a network interface or adapter to one or more remote devices, such as a remote computer. The remote computer may be a personal computer, a server, a router, a network PC, a peer device or other common network node, and typically includes many or all of the elements described above relative to the computer 300. The logical connections include one or more local area networks (LAN) and one or more wide area networks (WAN), but may also include other networks. Such networking environments are commonplace in offices, enterprise-wide computer networks, intranets and the Internet.

When used in a networked or cloud-computing environment, the computer may be connected to a public and/or private network through the network interface or adapter. In such embodiments, a modem or other means for establishing communications over the network is connected to the system bus via the network interface or adapter or other appropriate mechanism. A wireless networking component including an interface and antenna may be coupled through a suitable device such as an access point or peer computer to a network. In a networked environment, program modules depicted relative to the computer, or portions thereof, may be stored in the remote memory storage device.

The present disclosure also provides a method of estimating nutritional status of an individual of any age. The method generally includes the steps of measuring the circumference of a body part of an individual using a flexible elongate strip having a first scale of measurement indicia thereon and a second scale of indicia to provide a nutritional health standard score corresponding to the circumference for a selected age or age range, gender or designated population or combination thereof. In another form of the method, a flexible elongate strip is selected from a plurality of flexible elongate strips, each having a first scale of measurement indicia thereon and a second scale of indicia to provide a nutritional health standard score corresponding to the circumference of a body part for a selected age or age range, gender or designated population or combination thereof. A user selects a flexible elongate strip having a scale of indicia to provide a nutritional health standard score corresponding to the characteristics of the individual to be measured. In preferred forms, the scale of indicia for girth measurements are in 1 cm and 1 mm gradations or in 1 cm and 0.5 cm and 1 mm gradations. One particularly preferred scale for measuring the circumference or girth of the middle of the upper arm (the midpoint of the humerus) has 1 mm, 0.5 cm, and 1 cm gradations on the scale of indicia from 9.0 cm to 57.0 cm. Further, in this embodiment, the scale for measuring the standard score corresponding to the scale for measuring girth has gradations corresponding to standard scores of greater than −1, less than −1, less than −2 and less than −3 and less than 1, greater than 1, greater than 2 and greater than 3. Preferred body parts include the middle-upper arm, middle thigh, abdomen, and chest.

Advantageously, the methods of the present disclosure can also be adapted to estimate weight based on a variety of other measurements, and preferably other measurements of circumference or girth. In preferred forms, such other measurements include, but are not limited to the middle thigh, chest, and abdomen. When the middle thigh is used to estimate weight, the middle thigh circumference is preferably measured at the midpoint between the inguinal crease and the proximal border of the patella with the measurement being taken perpendicular to the long axis of the thigh. When the chest circumference is used to estimate weight, the circumference is preferably measured at the end of exhalation with the individual's arms extended outward and the tape or measurement positioned under the axilla, around wrapping around the chest at the level of the nipples. When abdominal circumference is used to estimate weight, the circumference is measured with the tape or measurement positioned in a horizontal plane at the level of the ilium wrapping just over the umbilicus. In each measurement, the measuring tape or device is preferably pulled snugly or contacted with the skin without compressing the skin.

BRIEF DESCRIPTION OF THE DRAWING FIGURES

The patent or application file contains at least one drawing executed in color. Copies of this patent or patent application publication with color drawing(s) will be provided by the Office upon request and payment of the necessary fee.

Figure 1:
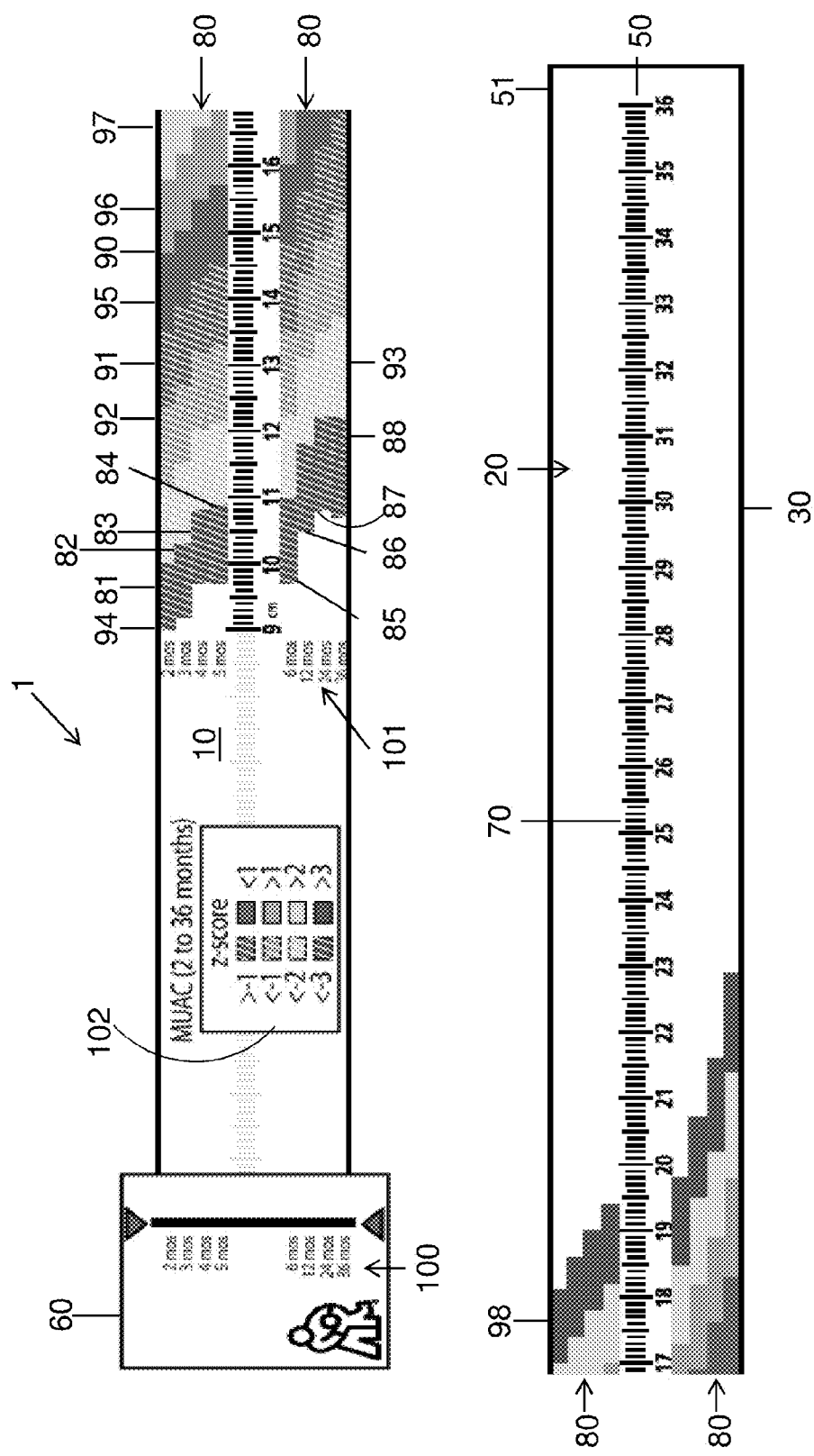
Figure 3:
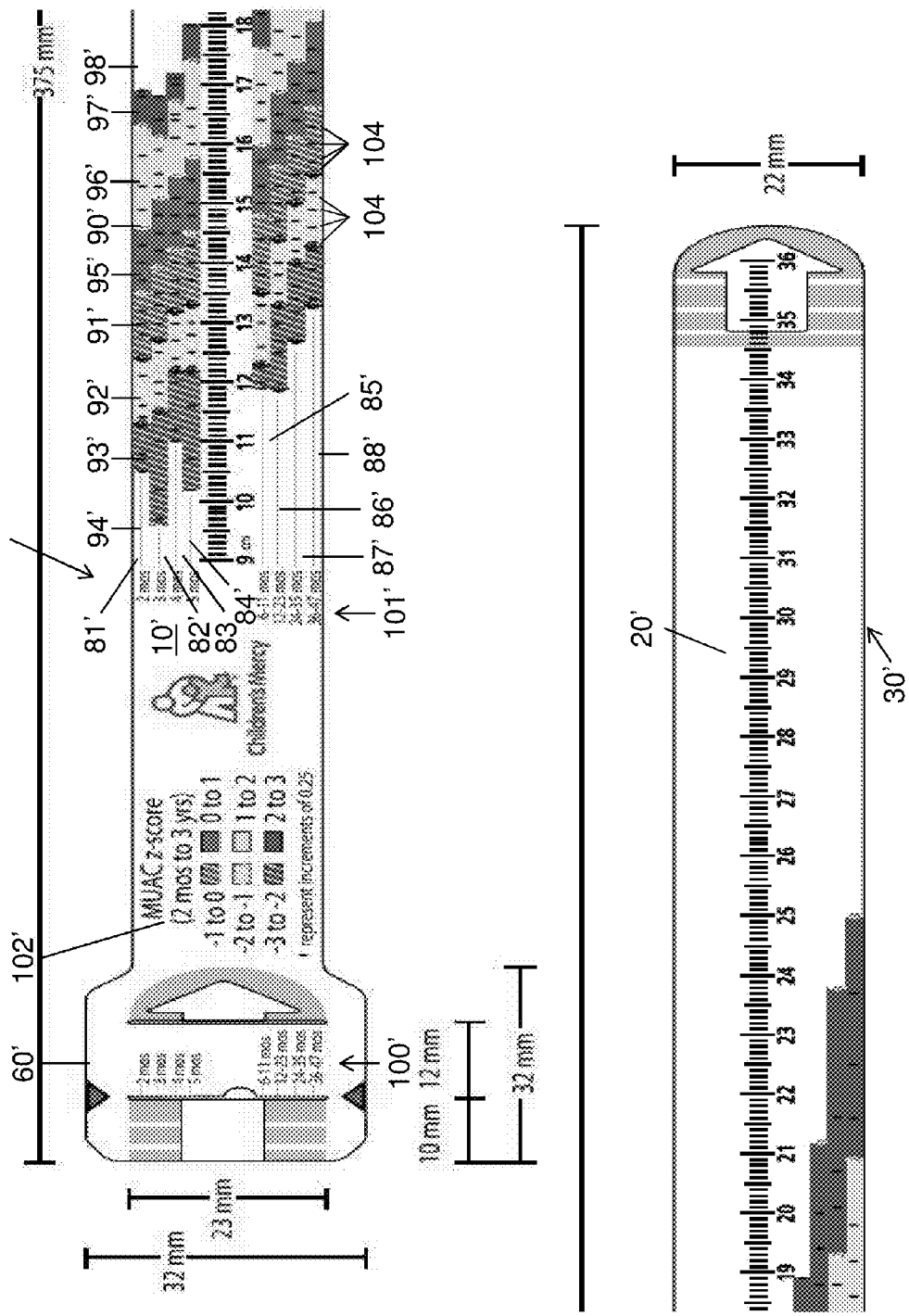
Figure 5:
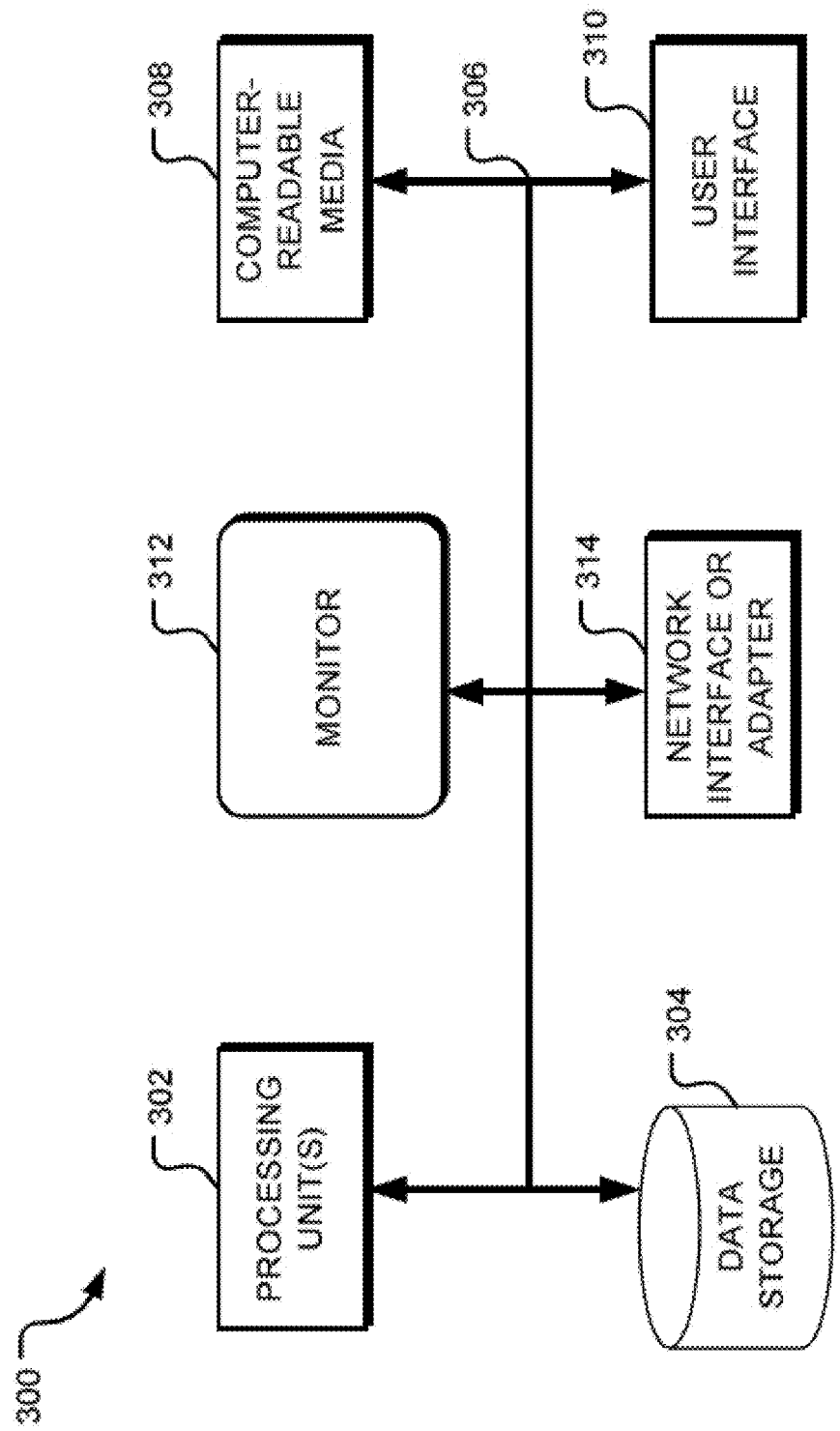

FIG. 1 is an illustration of a strip of one embodiment of the device of the present disclosure (MUAC z-score tape) for use on children aged 2 months to 47 months including standard score indicia that represent standard score ranges calculated from lambda, mu, and sigma (LMS) values that derive from population data that has been transformed and smoothed. The strip illustrated in FIG. 1 has been cut into two sections so that it fits onto a single page;

FIG. 2 is an illustration of another strip of one embodiment of the device for use on ages 4 years to 18 years including standard score indicia that represent standard score ranges calculated from lambda, mu, and sigma (LMS) values that derive from population data that has been transformed and smoothed. The strip illustrated in FIG. 2 has been cut into two sections so that it fits onto a single page;

FIG. 3 is an illustration of a strip of a second embodiment of the device for use on children aged 2 months to 47 months wherein the strip displays z-score ranges calculated to reflect the centiles for the raw untransformed data that correspond to selected z-scores as defined in standard normal probability tables. The strip illustrated in FIG. 3 has been cut into two sections so that it fits onto a single page;

FIG. 4 is an illustration of a strip of a second embodiment of the device for use on children aged 4 to 18 years wherein the strip displays z-score ranges calculated to reflect the centiles for the raw untransformed data that correspond to selected z-scores as defined in standard normal probability table. The strip illustrated in FIG. 4 has been cut into three sections so that it fits onto a single page; and FIG. 5 is a diagrammatic representation of an electronic embodiment of the device.

DETAILED DESCRIPTION

In one preferred embodiment of the present disclosure, illustrated in FIGS. 1 and 2, the device 1 comprises a plurality of elongate flexible strips 10, 11. The strips are of similar construction and unless otherwise indicated, each reference numeral applies to both strips. The strips 10 and 11 each have a respective first side 20 and an opposing second side 30, each of which includes imprinted indicia. The strips also each have a respective first end 40 and a second end 50. The first end 40 includes a fastener member 60, which may or may not be of unitary construction with the strip. The fastener 60 is sized and shaped to extend laterally beyond the sides of the strip sufficient to include an opening 61 such as a slit or slot 61. The slot 61 is positioned orthogonal to the strip and is sized for sliding reception of the second end 50 of the strip, thereby forming the strip 10 into a band for encircling a body part of an individual. The second end of each strip may be shaped at the sides to form a slightly narrower tip 51 for ease of insertion into the slot 61. The fastener members 60 and the respective strips 10 and 11 may be of unitary construction, or the fasteners may be formed separately and attached to form the first end 40 of the respective strip. Preferred body parts include the middle-upper arm, middle thigh, abdomen, and chest.

The first and second sides 20, 30 of the strips are each imprinted with two types of scales of indicia. A first scale of linear measurement indicia 70 includes a linear measurement scale marked with 1 mm, 0.5 mm and 1 cm gradations for measuring the circumference of a body part of an individual. The gradations may extend from 0 cm to 100 cm depending on the anticipated girth of body part of the individuals to be measured. Strip 10 is designed for use in individuals aged 2 months to 36 months, and includes gradations from 8 cm to 36 cm. Strip 11 is designed for individuals aged 4 years to 18 years and includes gradations from 9 cm to 57 cm. Preferred body parts include the middle-upper arm, middle thigh, abdomen, and chest. With specific reference to FIGS. 1-4, the strips and scales thereon are particularly adapted for instances when the body part is the middle upper arm.

Scales of standard score indicia 80 corresponding to preselected ages or age ranges are arranged in stacked relation above and/or below the first scale of indicia 70. The standard score indicia 80 can represent standard score ranges calculated from lambda, mu, and sigma (LMS) values that derive from population data that has been transformed and smoothed as previously described. Alternatively, the demarcated ranges can reflect the centiles for the raw untransformed data that correspond to selected standard scores as defined in standard normal probability tables. The standard score indicia scales 80 include a plurality of age or age range-specific scales of indicia, each of which indicates the range of linear measurements corresponding to a respective number of standard deviations from the mean measurement associated with nutritional status. For example, on strip 11 a first standard score indicia scale 81 represents standard scores for children aged 2 months. A second standard score indicia scale 82 represents standard scores for children aged 3 months. A third standard score indicia scale 83 represents standard scores for children aged 4 months. A fourth standard score indicia scale 84 represents standard scores for children aged 5 months. A fifth standard score indicia scale 85 represents standard scores for children aged 6 to 11 months. A sixth standard score indicia scale 86 represents standard scores for children aged 12 to 23 months. A seventh standard score indicia scale 87 represents standard scores for children aged 24 to 35 months. A second standard score indicia scale 88 represents standard scores for children aged 36 to 47 months.

The scales of standard score indicia each include groups of different indicia, each of which groups indicates the range of linear measurements corresponding to the norm and a respective number of standard deviations from the mean measurement associated with normal nutritional status. For example, a standard score of 1 for nutritional health is indicated by the reference numeral 90. A standard score greater than −1 for nutritional health (between the mean and 1 standard deviation below the mean) is indicated by the reference numeral 91. A standard score less than −1 (between 1 and 2 standard deviations below the mean) is indicated by the reference numeral 92. A standard score less than −2 (between 2 and 3 standard deviations below the mean) is indicated by the reference numeral 93. A standard score less than −3 (greater than 3 standard deviations below the mean) is indicated by the reference numeral 94. A standard score less than 1 (between the mean and 1 standard deviation above the mean) is indicated by the reference numeral 95. A standard score greater than 1 (between 1 and 2 standard deviations above the mean) is indicated by the reference numeral 96. A standard score greater than 2 (between 2 and 3 standard deviations above the mean) is indicated by the reverence numeral 97. A standard score greater than 3 (greater than 3 standard deviations above the mean) is indicated by the reference numeral 98.

An age key 100 is provided adjacent the slot 61 and is positioned so that each standard score indicia scale aligns with the corresponding age indicium when the circumference measurement of the body part is taken. An additional age key 101 is provided adjacent the ends of the standard score indicia scales at the lower end of the measurement indicia scale. A standard score or z-score key 102 may be provided in any open location, preferably between the fastener member 60 and the commencement of the scales 70 and 80. Preferred body parts include the middle-upper arm, middle thigh, abdomen, and chest. With specific reference to FIGS. 1-4, the scales thereon are particularly adapted for circumferential measurements of the middle-upper arm.

In use, an investigator selects a strip 10 designed to reflect data for the individual to be screened, e.g., according to age or age range, gender, or population group. Next, the investigator determines the body part they are going to measure and measures the circumference thereof as described herein. Preferred body parts include the middle-upper arm, middle thigh, abdomen, and chest. In one embodiment, the measurement taken is the midpoint of the upper arm, that is, the midpoint between the tip of the shoulder and the tip of the elbow of the individual to be measured. The investigator may wrap the strip 10 around the arm at the midpoint and then insert the second end of the strip into the slot 61 in the fastener portion 60 to encircle the arm. Alternatively, the investigator may insert the second end of the strip into the slot 61 to form a circle, which is then slid up the arm to its midpoint. When the strip has been positioned to encircle the midpoint of the upper arm, the investigator pulls on the free end of the strip to snug it against the arm of the individual. The margin of the slot overlying the indicia serves as an indicator or cursor to assist the investigator in reading the numeric measurement and standard score from the respective scales imprinted on the strip. In this manner, an investigator can simultaneously obtain both a middle-upper arm circumference measurement as well as the individual's standard or z-score for nutritional status, without the need to perform any further calculation or reference any table or chart.

A second preferred embodiment of the present disclosure is illustrated in FIGS. 3 and 4 to display z-score ranges calculated to reflect the centiles for the raw untransformed data that correspond to selected z-scores as defined in standard normal probability tables. FIGS. 3 and 4 depict parts in common with FIGS. 1 and 2 designated by corresponding reference numerals with the prime symbol ('). Additionally, FIGS. 3 and 4 include demarcations 104 within each standard score. These demarcations provide mathematical quartile distributions within each standard score. It is understood that these quartiles can be evenly or unevenly distributed. Further, although mathematical quartiles are shown in the figure, it is understood that those of skill in the art would also be able to construct and use other even and uneven distributions within each standard score. For example, $\frac{1}{10}^{th}$, or $\frac{1}{100}^{th}$ standard score value gradations could also be used.

FIG. 5 illustrates an example of a suitable computing and networking environment 300 that may be used to implement various aspects of the present disclosure described in FIGS. 1-4. As illustrated, the computing and networking environment 300 includes a general purpose computing device 300, although it is contemplated that the networking environment 300 may include other computing systems, such as personal computers, server computers, hand-held or laptop devices, tablet devices, multiprocessor systems, microprocessor-based systems, set top boxes, programmable consumer electronic devices, network PCs, minicomputers, mainframe computers, digital signal processors, state machines, logic circuitries, distributed computing environments that include any of the above computing systems or devices, and the like.

Components of the computer 300 may include various hardware components, such as a processing unit 302, a data storage 304 (e.g., a system memory), and a system bus 306 that couples various system components of the computer 300 to the processing unit 302. The system bus 306 may be any of several types of bus structures including a memory bus or memory controller, a peripheral bus, and a local bus using any of a variety of bus architectures. For example, such architectures may include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

The computer 300 may further include a variety of computer-readable media 308 that includes removable/non-removable media and volatile/nonvolatile media, but excludes transitory propagated signals. Computer-readable media 308 may also include computer storage media and communication media. Computer storage media includes removable/non-removable media and volatile/nonvolatile media implemented in any method or technology for storage of information, such as computer-readable instructions, data structures, program modules or other data, such as RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that may be used to store the desired information/data and which may be accessed by the computer 300. Communication media includes computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. For example, communication media may include wired media such as a wired network or direct-wired connection and wireless media such as acoustic, RF, infrared, and/or other wireless media, or some combination thereof. Computer-readable media may be embodied as a computer program product, such as software stored on computer storage media.

The data storage or system memory 304 includes computer storage media in the form of volatile/nonvolatile memory such as read only memory (ROM) and random access memory (RAM). A basic input/output system (BIOS), containing the basic routines that help to transfer information between elements within the computer 300 (e.g., during start-up) is typically stored in ROM. RAM typically contains data and/or program modules that are immediately accessible to and/or presently being operated on by processing unit 302. For example, in one embodiment, data storage 304 holds an operating system, application programs, and other program modules and program data.

Data storage 304 may also include other removable/non-removable, volatile/nonvolatile computer storage media. For example, data storage 304 may be: a hard disk drive that reads from or writes to non-removable, nonvolatile magnetic media; a magnetic disk drive that reads from or writes to a removable, nonvolatile magnetic disk; and/or an optical disk drive that reads from or writes to a removable, nonvolatile optical disk such as a CD-ROM or other optical media. Other removable/non-removable, volatile/nonvolatile computer storage media may include magnetic tape cassettes, flash memory cards, digital versatile disks, digital video tape, solid state RAM, solid state ROM, and the like. The drives and their associated computer storage media, described above and illustrated in FIG. 3, provide storage of computer-readable instructions, data structures, program modules and other data for the computer 300.

A user may enter commands and information through a user interface 310 or other input devices such as a tablet, electronic digitizer, a microphone, keyboard, and/or pointing device, commonly referred to as mouse, trackball or touch pad. Other input devices may include a joystick, game pad, satellite dish, scanner, or the like. Additionally, voice inputs, gesture inputs (e.g., via hands or fingers), or other natural user interfaces may also be used with the appropriate input devices, such as a microphone, camera, tablet, touch pad, glove, or other sensor. These and other input devices are often connected to the processing unit 302 through a user interface 310 that is coupled to the system bus 306, but may be connected by other interface and bus structures, such as a parallel port, game port or a universal serial bus (USB). A monitor 312 or other type of display device is also connected to the system bus 306 via an interface, such as a video interface. The monitor 312 may also be integrated with a touch-screen panel or the like.

The computer 300 may operate in a networked or cloud-computing environment using logical connections of a network interface or adapter 314 to one or more remote devices, such as a remote computer. The remote computer may be a personal computer, a server, a router, a network PC, a peer device or other common network node, and typically includes many or all of the elements described above relative to the computer 300. The logical connections depicted in FIG. 3 include one or more local area networks (LAN) and one or more wide area networks (WAN), but may also include other networks. Such networking environments are commonplace in offices, enterprise-wide computer networks, intranets and the Internet.

When used in a networked or cloud-computing environment, the computer 300 may be connected to a public and/or private network through the network interface or adapter 314. In such embodiments, a modem or other means for establishing communications over the network is connected to the system bus 306 via the network interface or adapter 314 or other appropriate mechanism. A wireless networking component including an interface and antenna may be coupled through a suitable device such as an access point or peer computer to a network. In a networked environment, program modules depicted relative to the computer 300, or portions thereof, may be stored in the remote memory storage device.

As can be appreciated, the figures and description above, are particularly well-suited for use with manual measurements using strips as described for the middle upper arm circumference. It is understood that the same data used to generate the standard scores can be provided in an electronic measurement device as well as for other body parts as described above. In use, electronic devices in accordance with the present disclosure would measure circumference by recording the distance traveled by a ball, roller, laser, or the like, as it was placed on the skin of the body part and moved about the circumference of the body part. In another embodiment of an electronic device, the device includes a measuring tape that can be wrapped about the circumference of the body part to be measured. The measuring tape is then drawn up against the body part by means of a retraction mechanism which can be manual, automated, or even electronically controlled. The measurement is then recorded by the device using conventional means and correlated with the scales in order to automatically determine nutritional status.

Definitions

A "child" or "children" for purposes of the present disclosure include any person from birth to 18 years of age. The present disclosure includes a preferred embodiment where the device of the present disclosure is suitable for children from 2 months to 18 years of age.

A "measurement" for purposes of the present disclosure refers to the use of a device to determine a value. The value can be circumference or girth, etc.

"Indicia" for purposes of the present disclosure refers to letters, numbers, symbols, colors, and patterns.

"Mean" and "median" for purposes of the present disclosure refer to a reference value that represents the central tendency. These terms are used interchangeably unless otherwise indicated.

"MUAC Z-score tape" for purposes of the present disclosure refers to one embodiment of the device of the present disclosure wherein the middle upper arm circumference is the body part measured.

A "scale" for purposes of the present disclosure refers to a set of values, numbers, or indicia that represent values used to obtain the estimated weight or dose. Alternately, a scale can be a physical weight measuring machine, depending on the context in which the word "scale" is used.

A "standard score" or "z-score" for purposes of the present disclosure refers to the number of standard deviations the body part circumference measurement is above or below a standard reference body part circumference measurement for a reference population that is associated with nutritional health, with a standard score of 0.0 indicating the norm, negative standard scores indicating below −1.0 and positive standard scores above 1.0 indicating scores outside the body part circumference measurement associated with nutritional health.

A "strip", for purposes of the present disclosure, refers to a rectangular shaped segment of material that is longer than it is wide. A strip in the context of the present disclosure is part of the device of the present disclosure.

EXAMPLES

The following examples are provided for illustrative purposes only. Nothing contained herein shall be construed as a limitation of the scope of the present disclosure.

Example 1

This example illustrates a method of using the device of the present disclosure to estimate nutritional status using the middle upper arm circumference.
Materials and Methods An embodiment of the device of the present disclosure incorporating one strip that will be printed on both sides is used, wherein one side had a scale for girth and a scale for standard scores for females and the other side had a scale for girth and a scale for standard scores for males.

The side of the strip printed with a scale for female girth is used to measure the middle-upper arm circumference of a female. This value is recorded, along with the corresponding standard score which is read from the strip. The side of the strip printed with a scale for male girth is used to measure the middle-upper arm circumference of a male. This value is recorded, along with the corresponding standard score which is read from the strip. The score of the female is used to inform the decision to institute nutritional support for treatment of malnutrition. The score of the male is used to inform the decision to conduct further testing to determine whether obesity-based malnutrition may be present.
Results and Discussion Because the standard score for the female is less than −2, the female is undernourished. Because the standard score for the male is greater than 3, the male is also at risk for malnutrition based on overweight or obesity. Because obesity can be an indicator for malnutrition, the male is referred for further evaluation.

Example 2

This example illustrates a method of using centiles corresponding to a specified z-score range as derived from the standard probability table to demarcate the percent of the reference population that falls within the MUAC z-score tape zones.
Methods For a reference population wherein the MUAC values are not normally distributed (e.g. skewness >0.5, kurtosis >1.0) and there has been no transformation to symmetry or smoothing of the data, the MUAC z-score tape zones can be demarcated by the centiles that correspond to a specified z-score range as derived from the standard normal probability table (provided below in Table 1). For example; a z-score range from −1.50 to −1.75 would be represented by the MUAC values for the lower 6.68% and 4.01% of the population, respectively.

The scales of standard score indicia each include groups of different indicia, each of which groups indicates the range of linear measurements corresponding to the norm and a respective number of standard deviations from the median measurement associated with normal nutritional status. Referring now to FIGS. 3 and 4, for example, a standard score of 1 for nutritional health corresponding to the 84.13 centile is indicated by the reference numeral 90'. A standard score greater than −1 for nutritional health (between the 15.87 and 50.00 centile) is indicated by the reference numeral 91'. A standard score less than −1 (between the 2.28 and 15.87 centiles) is indicated by the reference numeral 92'. A standard score less than −2 (between the 1.30 and 2.28 centiles) is indicated by the reference numeral 93'. A standard score less than −3 (less than the 1.00 centile) is indicated by the reference numeral 94'. A standard score less than 1 (between the 50.00 and 84.13 centile) is indicated by the reference numeral 95'. A standard score greater than 1 (between the 84.13 and 97.72 centiles) is indicated by the reference numeral 96'. A standard score greater than 2 (between the 97.72 and 99.87 centiles) is indicated by the reference numeral 97'. A standard score greater than 3 (greater than 99.87 centile) is indicated by the reference numeral 98'. Quarter z-scores are also shown on FIGS. 3 and 4 by the reference numeral 104'.

TABLE 1

Standard Normal Probabilities

| z | .00 | .01 | .02 | .03 | .04 | .05 | .06 | .07 | .08 | .09 |
|---|---|---|---|---|---|---|---|---|---|---|
| −3.4 | 0.03% | 0.03% | 0.03% | 0.03% | 0.03% | 0.03% | 0.03% | 0.03% | 0.03% | 0.02% |
| −3.3 | 0.05% | 0.05% | 0.05% | 0.04% | 0.04% | 0.04% | 0.04% | 0.04% | 0.04% | 0.03% |
| −3.2 | 0.07% | 0.07% | 0.06% | 0.06% | 0.06% | 0.06% | 0.06% | 0.05% | 0.05% | 0.05% |
| −3.1 | 0.10% | 0.09% | 0.09% | 0.09% | 0.08% | 0.08% | 0.08% | 0.08% | 0.07% | 0.07% |
| −3.0 | 0.13% | 0.13% | 0.13% | 0.12% | 0.12% | 0.11% | 0.11% | 0.11% | 0.10% | 0.10% |
| −2.9 | 0.19% | 0.18% | 0.18% | 0.17% | 0.16% | 0.16% | 0.15% | 0.15% | 0.14% | 0.14% |
| −2.8 | 0.26% | 0.25% | 0.24% | 0.23% | 0.23% | 0.22% | 0.21% | 0.21% | 0.20% | 0.19% |
| −2.7 | 0.35% | 0.34% | 0.33% | 0.32% | 0.31% | 0.30% | 0.29% | 0.28% | 0.27% | 0.26% |
| −2.6 | 0.47% | 0.45% | 0.44% | 0.43% | 0.41% | 0.40% | 0.39% | 0.38% | 0.37% | 0.36% |
| −2.5 | 0.62% | 0.60% | 0.59% | 0.57% | 0.55% | 0.54% | 0.52% | 0.51% | 0.49% | 0.48% |
| −2.4 | 0.82% | 0.80% | 0.78% | 0.75% | 0.73% | 0.71% | 0.69% | 0.68% | 0.66% | 0.64% |
| −2.3 | 1.07% | 1.04% | 1.02% | 0.99% | 0.96% | 0.94% | 0.91% | 0.89% | 0.87% | 0.84% |
| −2.2 | 1.39% | 1.36% | 1.32% | 1.29% | 1.25% | 1.22% | 1.19% | 1.16% | 1.13% | 1.10% |
| −2.1 | 1.79% | 1.74% | 1.70% | 1.66% | 1.62% | 1.58% | 1.54% | 1.50% | 1.46% | 1.43% |
| −2.0 | 2.28% | 2.22% | 2.17% | 2.12% | 2.07% | 2.02% | 1.97% | 1.92% | 1.88% | 1.83% |
| −1.9 | 2.87% | 2.81% | 2.74% | 2.68% | 2.62% | 2.56% | 2.50% | 2.44% | 2.39% | 2.33% |
| −1.8 | 3.59% | 3.51% | 3.44% | 3.36% | 3.29% | 3.22% | 3.14% | 3.07% | 3.01% | 2.94% |
| −1.7 | 4.46% | 4.36% | 4.27% | 4.18% | 4.09% | 4.01% | 3.92% | 3.84% | 3.75% | 3.67% |
| −1.6 | 5.48% | 5.37% | 5.26% | 5.16% | 5.05% | 4.95% | 4.85% | 4.75% | 4.65% | 4.55% |
| −1.5 | 6.68% | 6.55% | 6.43% | 6.30% | 6.18% | 6.06% | 5.94% | 5.82% | 5.71% | 5.59% |

TABLE 1-continued

Standard Normal Probabilities

| z | .00 | .01 | .02 | .03 | .04 | .05 | .06 | .07 | .08 | .09 |
|---|---|---|---|---|---|---|---|---|---|---|
| −1.4 | 8.08% | 7.93% | 7.78% | 7.64% | 7.49% | 7.35% | 7.21% | 7.08% | 6.94% | 6.81% |
| −1.3 | 9.68% | 9.51% | 9.34% | 9.18% | 9.01% | 8.85% | 8.69% | 8.53% | 8.38% | 8.23% |
| −1.2 | 11.51% | 11.31% | 11.12% | 10.93% | 10.75% | 10.56% | 10.38% | 10.20% | 10.03% | 9.85% |
| −1.1 | 13.57% | 13.35% | 13.14% | 12.92% | 12.71% | 12.51% | 12.30% | 12.10% | 11.90% | 11.70% |
| −1.0 | 15.87% | 15.62% | 15.39% | 15.15% | 14.92% | 14.69% | 14.46% | 14.23% | 14.01% | 13.79% |
| −0.9 | 18.41% | 18.14% | 17.88% | 17.62% | 17.36% | 17.11% | 16.85% | 16.60% | 16.35% | 16.11% |
| −0.8 | 21.19% | 20.90% | 20.61% | 20.33% | 20.05% | 19.77% | 19.49% | 19.22% | 18.94% | 18.67% |
| −0.7 | 24.20% | 23.89% | 23.58% | 23.27% | 22.96% | 22.66% | 22.36% | 22.06% | 21.77% | 21.48% |
| −0.6 | 27.43% | 27.09% | 26.76% | 26.43% | 26.11% | 25.78% | 25.46% | 25.14% | 24.83% | 24.51% |
| −0.5 | 30.85% | 30.50% | 30.15% | 29.81% | 29.46% | 29.12% | 28.77% | 28.43% | 28.10% | 27.76% |
| −0.4 | 34.46% | 34.09% | 33.72% | 33.36% | 33.00% | 32.64% | 32.28% | 31.92% | 31.56% | 31.21% |
| −0.3 | 38.21% | 37.83% | 37.45% | 37.07% | 36.69% | 36.32% | 35.94% | 35.57% | 35.20% | 34.83% |
| −0.2 | 42.07% | 41.68% | 41.29% | 40.90% | 40.52% | 40.13% | 39.74% | 39.36% | 38.97% | 38.59% |
| −0.1 | 46.02% | 45.62% | 45.22% | 44.83% | 44.43% | 44.04% | 43.64% | 43.25% | 42.86% | 42.47% |
| −0.0 | 50.00% | 49.60% | 49.20% | 48.80% | 48.40% | 48.01% | 47.61% | 47.21% | 46.81% | 46.41% |
| 0.0 | 50.00% | 50.40% | 50.80% | 51.20% | 51.60% | 51.99% | 52.39% | 52.79% | 53.19% | 53.59% |
| 0.1 | 53.98% | 54.38% | 54.78% | 55.17% | 55.57% | 55.96% | 56.36% | 56.75% | 57.14% | 57.53% |
| 0.2 | 57.93% | 58.32% | 58.71% | 59.10% | 59.48% | 59.87% | 60.26% | 60.64% | 61.03% | 61.41% |
| 0.3 | 61.79% | 62.17% | 62.55% | 62.93% | 63.31% | 63.68% | 64.06% | 64.43% | 64.80% | 65.17% |
| 0.4 | 65.54% | 65.91% | 66.28% | 66.64% | 67.00% | 67.36% | 67.72% | 68.08% | 68.44% | 68.79% |
| 0.5 | 69.15% | 69.50% | 69.85% | 70.19% | 70.54% | 70.88% | 71.23% | 71.57% | 71.90% | 72.24% |
| 0.6 | 72.57% | 72.91% | 73.24% | 73.57% | 73.89% | 74.22% | 74.54% | 74.86% | 75.17% | 75.49% |
| 0.7 | 75.80% | 76.11% | 76.42% | 76.73% | 77.04% | 77.34% | 77.64% | 77.94% | 78.23% | 78.52% |
| 0.8 | 78.81% | 79.10% | 79.39% | 79.67% | 79.95% | 80.23% | 80.51% | 80.78% | 81.06% | 81.33% |
| 0.9 | 81.59% | 81.86% | 82.12% | 82.38% | 82.64% | 82.89% | 83.15% | 83.40% | 83.65% | 83.89% |
| 1.0 | 84.13% | 84.38% | 84.61% | 84.85% | 85.08% | 85.31% | 85.54% | 85.77% | 85.99% | 86.21% |
| 1.1 | 86.43% | 86.65% | 86.86% | 87.08% | 87.29% | 87.49% | 87.70% | 87.90% | 88.10% | 88.30% |
| 1.2 | 88.49% | 88.69% | 88.88% | 89.07% | 89.25% | 89.44% | 89.62% | 89.80% | 89.97% | 90.15% |
| 1.3 | 90.32% | 90.49% | 90.66% | 90.82% | 90.99% | 91.15% | 91.31% | 91.47% | 91.62% | 91.77% |
| 1.4 | 91.92% | 92.07% | 92.22% | 92.36% | 92.51% | 92.65% | 92.79% | 92.92% | 93.06% | 93.19% |
| 1.5 | 93.32% | 93.45% | 93.57% | 93.70% | 93.82% | 93.94% | 94.06% | 94.18% | 94.29% | 94.41% |
| 1.6 | 94.52% | 94.63% | 94.74% | 94.84% | 94.95% | 95.05% | 95.15% | 95.25% | 95.35% | 95.45% |
| 1.7 | 95.54% | 95.64% | 95.73% | 95.82% | 95.91% | 95.99% | 96.08% | 96.16% | 96.25% | 96.33% |
| 1.8 | 96.41% | 96.49% | 96.56% | 96.64% | 96.71% | 96.78% | 96.86% | 96.93% | 96.99% | 97.06% |
| 1.9 | 97.13% | 97.19% | 97.26% | 97.32% | 97.38% | 97.44% | 97.50% | 97.56% | 97.61% | 97.67% |
| 2.0 | 97.72% | 97.78% | 97.83% | 97.88% | 97.93% | 97.98% | 98.03% | 98.08% | 98.12% | 98.17% |
| 2.1 | 98.21% | 98.26% | 98.30% | 98.34% | 98.38% | 98.42% | 98.46% | 98.50% | 98.54% | 98.57% |
| 2.2 | 98.61% | 98.64% | 98.68% | 98.71% | 98.75% | 98.78% | 98.81% | 98.84% | 98.87% | 98.90% |
| 2.3 | 98.93% | 98.96% | 98.98% | 99.01% | 99.04% | 99.06% | 99.09% | 99.11% | 99.13% | 99.16% |
| 2.4 | 99.18% | 99.20% | 99.22% | 99.25% | 99.27% | 99.29% | 99.31% | 99.32% | 99.34% | 99.36% |
| 2.5 | 99.38% | 99.40% | 99.41% | 99.43% | 99.45% | 99.46% | 99.48% | 99.49% | 99.51% | 99.52% |
| 2.6 | 99.53% | 99.55% | 99.56% | 99.57% | 99.59% | 99.60% | 99.61% | 99.62% | 99.63% | 99.64% |
| 2.7 | 99.65% | 99.66% | 99.67% | 99.68% | 99.69% | 99.70% | 99.71% | 99.72% | 99.73% | 99.74% |
| 2.8 | 99.74% | 99.75% | 99.76% | 99.77% | 99.77% | 99.78% | 99.79% | 99.79% | 99.80% | 99.81% |
| 2.9 | 99.81% | 99.82% | 99.82% | 99.83% | 99.84% | 99.84% | 99.85% | 99.85% | 99.86% | 99.86% |
| 3.0 | 99.87% | 99.87% | 99.87% | 99.88% | 99.88% | 99.89% | 99.89% | 99.89% | 99.90% | 99.90% |
| 3.1 | 99.90% | 99.91% | 99.91% | 99.91% | 99.92% | 99.92% | 99.92% | 99.92% | 99.93% | 99.93% |
| 3.2 | 99.93% | 99.93% | 99.94% | 99.94% | 99.94% | 99.94% | 99.94% | 99.95% | 99.95% | 99.95% |
| 3.3 | 99.95% | 99.95% | 99.95% | 99.96% | 99.96% | 99.96% | 99.96% | 99.96% | 99.96% | 99.97% |
| 3.4 | 99.97% | 99.97% | 99.97% | 99.97% | 99.97% | 99.97% | 99.97% | 99.97% | 99.97% | 99.98% |

Conclusion

Demarcation of the centiles that correspond to specified z-score range in this manner provides a z-score tape that includes additional necessary information for use with reference populations where the MUAC measurement values are not normally distributed.

Middle-upper arm circumference in conjunction with data on established standard scores for nutritional health in a reference population based on age, gender and ethnicity address a critical medical need in settings where populations must be screened with portable devices that are simple to use, require minimal training and provide results that are visually displayed without the need for further calculation or interpretation from reference tables or charts. To date, no single previous device or method has provided accurate estimates of nutritional status across a broad range of ages, and populations for both genders. The MUAC Z-score device and method attempts to address limitations inherent in the existing nutritional status estimation strategies. It expands the age range of individuals to which a single nutritional status estimation method can be applied and expands the screenable population to include individuals who are overweight or obese but may suffer from malnutrition.

Example 3

This example illustrates a method of using LMS corresponding to a specified z-score range as derived from the standard probability table to demarcate the percent of the reference population that falls within the MUAC z-score tape zones.

Methods

Anthropometric data for model development were obtained from the Centers for Disease Control and Prevention (CDC) National Health and Nutrition Examination Survey (NHANES). Data from 1999-2012 were downloaded and datasets for children 2 months through 18 years of age extracted into a separate database. Incomplete datasets and those missing the relevant variables were excluded. MUAC outliers that might be the result of measurement error were identified by application of the modified Thompson tau test. Data were segregated by gender and mean ($\bar{x}$) and standard deviation ($\sigma$) MUAC were calculated at each month of age. The absolute deviation for each data point ($\delta i$) was determined according to $\delta i=|xi-\bar{x}|$. The modified Thompson tau value was calculated according to $\tau=[t\alpha/2*(n-1)]/[\sqrt{n}*\sqrt{(n-2+t\alpha/22)}]$ where n is the number of data points and $t\alpha/2$ is the student's t value based on a highly conservative $\alpha$ value of 0.001 with n–2 degrees of freedom. The individual sample with the largest $\delta i$ value was rejected when $\delta i > \tau*\sigma$. Subsequently $\bar{x}$ and $\sigma$ were recalculated and recursive elimination was used to remove each successive maximum $\delta i$ value until no additional outliers were identified (i.e. $\delta i \le \tau*\sigma$). To avoid introducing imprecision with smaller than recommended sample sizes, selected age groups were pooled in a similar fashion to the groupings used by the CDC in the construction of their 2000 growth charts. Data for children 1 year of age and over were pooled in 6 month intervals. Data from children 2-11 months of age were retained in 10 distinct age groups and weighted to limit bias in fitting toward the older age groups. Though the sample sizes were smaller for this infant population, estimates of skewness and kurtosis confirmed a near normal distribution. Independently collected data from 2 different U.S. studies were used for validation. These investigations were reviewed and approved by the Institutional Review Board at Children's Mercy Hospital. Comparisons were also made to earlier published MUAC centiles from the 1971-1974 and 1988-1994 surveys. Gender-specific growth curves were created using the Lambda Mu Sigma method described by Cole and Green, and executed with LMSchartmaker Pro v2.54 (Harlow Pronting Limited, Tyne & Wear, UK). The distribution of MUAC values were summarized for each age group using age-specific Box-Cox power transformation of skewness (L), median (M), and coefficient of variation (S). This method transforms the anthropometric data so that they are approximately normally distributed and generates age-specific estimates of LMS as cubic smoothing splines by nonlinear regression. Maximum penalized likelihood estimation was used to optimize the effective degrees of freedom (edf) for M followed by L and then S. Goodness-of-fit was assessed by examining 1) plots of the fitted centiles overlaid on the empirical centiles, 2) the detrended quantile-quantile (Q-Q) plots of the z-scores with their corresponding worm plots, 3) the Q statistics for L, M, S, and kurtosis, and 4) the mean and standard deviation of z-scores at each age group. The newly created LMS values were applied to data from a population of children wherein MUAC was obtained as part of a larger anthropometric survey. For each child, gender- and age-specific z-score was calculated according to $zi=(((xi/M)^L)-1)/(LS)$. Where zi represents the individual z-score, xi the individual MUAC value, and LMS the lambda, mu, and sigma values, respectively. For cases where L=0, z-score was calculated according to $zi=\ln(xi/M)/S$. The data were stratified into groups of sufficient sample size and the mean and standard deviation of z-scores at each age group was examined as described above. The distribution of weight-for-age z-scores was also examined for concordance with MUAC z-scores. Finally, the growth curves were compared with previously published data to examine trends in U.S. norms over the last 4 decades. All comparisons were performed in SPSS v23 (IBM, Armonk, N.Y.). Results are provided in Table 2. The values within Table 2 are well adapted for use within a database, and especially within a database used or accessed by an electric measurement device wherein the device measures a desired part, accesses the database contained therein, and provides the user with the z-score and/or weight.

TABLE 2

| Age (mos) | Males | | | Females | | |
|---|---|---|---|---|---|---|
| | L | M | S | L | M | S |
| 2 | 1.162 | 13.680 | 0.083 | −0.096 | 13.276 | 0.084 |
| 3 | 1.025 | 14.081 | 0.081 | −0.119 | 13.635 | 0.083 |
| 4 | 0.899 | 14.419 | 0.080 | −0.142 | 13.979 | 0.083 |
| 5 | 0.782 | 14.688 | 0.079 | −0.166 | 14.279 | 0.082 |
| 6 | 0.675 | 14.903 | 0.078 | −0.192 | 14.526 | 0.081 |
| 7 | 0.575 | 15.078 | 0.077 | −0.223 | 14.722 | 0.081 |
| 8 | 0.482 | 15.218 | 0.076 | −0.257 | 14.879 | 0.081 |
| 9 | 0.394 | 15.323 | 0.075 | −0.295 | 15.009 | 0.081 |
| 10 | 0.310 | 15.401 | 0.075 | −0.335 | 15.120 | 0.080 |
| 11 | 0.228 | 15.464 | 0.075 | −0.377 | 15.219 | 0.080 |
| 12 | 0.148 | 15.524 | 0.075 | −0.419 | 15.308 | 0.080 |
| 13 | 0.069 | 15.581 | 0.074 | −0.460 | 15.390 | 0.080 |
| 14 | −0.010 | 15.637 | 0.074 | −0.500 | 15.467 | 0.080 |
| 15 | −0.087 | 15.691 | 0.074 | −0.537 | 15.538 | 0.080 |
| 16 | −0.164 | 15.741 | 0.074 | −0.572 | 15.603 | 0.080 |
| 17 | −0.240 | 15.786 | 0.074 | −0.605 | 15.662 | 0.080 |
| 18 | −0.315 | 15.828 | 0.073 | −0.635 | 15.716 | 0.080 |
| 19 | −0.390 | 15.864 | 0.073 | −0.664 | 15.767 | 0.080 |
| 20 | −0.465 | 15.897 | 0.073 | −0.691 | 15.813 | 0.080 |
| 21 | −0.538 | 15.928 | 0.073 | −0.716 | 15.856 | 0.080 |
| 22 | −0.612 | 15.958 | 0.073 | −0.739 | 15.896 | 0.080 |
| 23 | −0.684 | 15.988 | 0.073 | −0.760 | 15.933 | 0.081 |
| 24 | −0.756 | 16.019 | 0.073 | −0.781 | 15.969 | 0.081 |
| 25 | −0.828 | 16.051 | 0.073 | −0.802 | 16.005 | 0.081 |
| 26 | −0.899 | 16.086 | 0.073 | −0.823 | 16.040 | 0.081 |
| 27 | −0.969 | 16.121 | 0.073 | −0.844 | 16.075 | 0.081 |
| 28 | −1.038 | 16.158 | 0.073 | −0.865 | 16.110 | 0.081 |
| 29 | −1.105 | 16.196 | 0.074 | −0.886 | 16.145 | 0.081 |
| 30 | −1.171 | 16.234 | 0.074 | −0.907 | 16.181 | 0.081 |
| 31 | −1.236 | 16.273 | 0.075 | −0.931 | 16.221 | 0.081 |
| 32 | −1.298 | 16.313 | 0.075 | −0.955 | 16.262 | 0.082 |
| 33 | −1.359 | 16.354 | 0.076 | −0.980 | 16.304 | 0.082 |
| 34 | −1.419 | 16.397 | 0.076 | −1.006 | 16.347 | 0.082 |
| 35 | −1.477 | 16.441 | 0.077 | −1.033 | 16.392 | 0.082 |
| 36 | −1.532 | 16.487 | 0.078 | −1.061 | 16.438 | 0.083 |
| 37 | −1.586 | 16.534 | 0.078 | −1.091 | 16.486 | 0.083 |
| 38 | −1.639 | 16.583 | 0.079 | −1.121 | 16.535 | 0.083 |
| 39 | −1.689 | 16.634 | 0.080 | −1.151 | 16.586 | 0.083 |
| 40 | −1.737 | 16.684 | 0.081 | −1.183 | 16.637 | 0.084 |
| 41 | −1.784 | 16.736 | 0.081 | −1.215 | 16.690 | 0.084 |
| 42 | −1.828 | 16.787 | 0.082 | −1.247 | 16.743 | 0.085 |
| 43 | −1.871 | 16.838 | 0.083 | −1.280 | 16.797 | 0.085 |
| 44 | −1.912 | 16.889 | 0.084 | −1.313 | 16.851 | 0.086 |
| 45 | −1.950 | 16.940 | 0.085 | −1.346 | 16.905 | 0.086 |
| 46 | −1.987 | 16.990 | 0.086 | −1.379 | 16.960 | 0.087 |
| 47 | −2.022 | 17.039 | 0.087 | −1.411 | 17.014 | 0.087 |
| 48 | −2.055 | 17.088 | 0.088 | −1.444 | 17.068 | 0.088 |
| 49 | −2.086 | 17.137 | 0.089 | −1.475 | 17.121 | 0.088 |
| 50 | −2.115 | 17.185 | 0.089 | −1.506 | 17.173 | 0.089 |
| 51 | −2.142 | 17.233 | 0.090 | −1.537 | 17.225 | 0.089 |
| 52 | −2.168 | 17.280 | 0.091 | −1.567 | 17.277 | 0.090 |
| 53 | −2.191 | 17.328 | 0.092 | −1.596 | 17.328 | 0.091 |
| 54 | −2.213 | 17.377 | 0.093 | −1.625 | 17.379 | 0.091 |
| 55 | −2.233 | 17.425 | 0.094 | −1.653 | 17.429 | 0.092 |
| 56 | −2.251 | 17.474 | 0.095 | −1.681 | 17.480 | 0.093 |
| 57 | −2.268 | 17.524 | 0.096 | −1.708 | 17.530 | 0.093 |
| 58 | −2.282 | 17.574 | 0.097 | −1.735 | 17.581 | 0.094 |
| 59 | −2.294 | 17.626 | 0.098 | −1.761 | 17.632 | 0.095 |
| 60 | −2.305 | 17.677 | 0.099 | −1.786 | 17.683 | 0.096 |
| 61 | −2.314 | 17.730 | 0.100 | −1.811 | 17.735 | 0.096 |
| 62 | −2.321 | 17.784 | 0.101 | −1.835 | 17.788 | 0.097 |
| 63 | −2.326 | 17.838 | 0.102 | −1.858 | 17.841 | 0.098 |
| 64 | −2.329 | 17.893 | 0.103 | −1.881 | 17.896 | 0.099 |
| 65 | −2.330 | 17.949 | 0.104 | −1.903 | 17.951 | 0.100 |
| 66 | −2.330 | 18.005 | 0.105 | −1.924 | 18.009 | 0.101 |
| 67 | −2.328 | 18.062 | 0.106 | −1.944 | 18.068 | 0.102 |
| 68 | −2.324 | 18.120 | 0.107 | −1.963 | 18.130 | 0.103 |
| 69 | −2.319 | 18.179 | 0.108 | −1.981 | 18.193 | 0.104 |
| 70 | −2.312 | 18.239 | 0.109 | −1.998 | 18.257 | 0.105 |
| 71 | −2.304 | 18.300 | 0.110 | −2.013 | 18.323 | 0.106 |

TABLE 2-continued

| Age (mos) | Males L | Males M | Males S | Females L | Females M | Females S |
|---|---|---|---|---|---|---|
| 72 | -2.294 | 18.363 | 0.112 | -2.026 | 18.391 | 0.107 |
| 73 | -2.284 | 18.427 | 0.113 | -2.038 | 18.460 | 0.108 |
| 74 | -2.271 | 18.493 | 0.114 | -2.048 | 18.531 | 0.109 |
| 75 | -2.258 | 18.561 | 0.115 | -2.056 | 18.604 | 0.111 |
| 76 | -2.243 | 18.631 | 0.116 | -2.062 | 18.679 | 0.112 |
| 77 | -2.227 | 18.702 | 0.117 | -2.066 | 18.756 | 0.113 |
| 78 | -2.210 | 18.775 | 0.119 | -2.069 | 18.835 | 0.114 |
| 79 | -2.192 | 18.849 | 0.120 | -2.068 | 18.917 | 0.116 |
| 80 | -2.173 | 18.925 | 0.121 | -2.066 | 19.002 | 0.117 |
| 81 | -2.152 | 19.002 | 0.122 | -2.061 | 19.088 | 0.118 |
| 82 | -2.131 | 19.080 | 0.123 | -2.054 | 19.177 | 0.120 |
| 83 | -2.109 | 19.160 | 0.124 | -2.044 | 19.267 | 0.121 |
| 84 | -2.085 | 19.240 | 0.125 | -2.032 | 19.358 | 0.123 |
| 85 | -2.061 | 19.322 | 0.126 | -2.017 | 19.450 | 0.124 |
| 86 | -2.036 | 19.404 | 0.127 | -1.999 | 19.543 | 0.125 |
| 87 | -2.010 | 19.486 | 0.129 | -1.979 | 19.636 | 0.127 |
| 88 | -1.984 | 19.570 | 0.130 | -1.957 | 19.730 | 0.128 |
| 89 | -1.956 | 19.654 | 0.131 | -1.932 | 19.825 | 0.130 |
| 90 | -1.929 | 19.738 | 0.132 | -1.905 | 19.920 | 0.131 |
| 91 | -1.900 | 19.824 | 0.133 | -1.877 | 20.016 | 0.133 |
| 92 | -1.872 | 19.909 | 0.134 | -1.847 | 20.113 | 0.134 |
| 93 | -1.843 | 19.996 | 0.135 | -1.816 | 20.209 | 0.135 |
| 94 | -1.814 | 20.083 | 0.136 | -1.783 | 20.307 | 0.137 |
| 95 | -1.785 | 20.170 | 0.137 | -1.748 | 20.405 | 0.138 |
| 96 | -1.755 | 20.258 | 0.138 | -1.713 | 20.504 | 0.139 |
| 97 | -1.726 | 20.347 | 0.139 | -1.676 | 20.604 | 0.141 |
| 98 | -1.697 | 20.436 | 0.140 | -1.639 | 20.704 | 0.142 |
| 99 | -1.668 | 20.525 | 0.141 | -1.601 | 20.806 | 0.143 |
| 100 | -1.639 | 20.615 | 0.142 | -1.562 | 20.908 | 0.144 |
| 101 | -1.611 | 20.706 | 0.143 | -1.523 | 21.010 | 0.145 |
| 102 | -1.582 | 20.797 | 0.144 | -1.483 | 21.114 | 0.146 |
| 103 | -1.555 | 20.889 | 0.145 | -1.443 | 21.219 | 0.148 |
| 104 | -1.527 | 20.982 | 0.146 | -1.403 | 21.324 | 0.149 |
| 105 | -1.500 | 21.076 | 0.147 | -1.363 | 21.429 | 0.150 |
| 106 | -1.473 | 21.170 | 0.148 | -1.323 | 21.535 | 0.151 |
| 107 | -1.447 | 21.264 | 0.149 | -1.285 | 21.641 | 0.151 |
| 108 | -1.421 | 21.360 | 0.150 | -1.247 | 21.746 | 0.152 |
| 109 | -1.395 | 21.456 | 0.150 | -1.210 | 21.851 | 0.153 |
| 110 | -1.370 | 21.552 | 0.151 | -1.175 | 21.955 | 0.154 |
| 111 | -1.346 | 21.650 | 0.152 | -1.141 | 22.059 | 0.155 |
| 112 | -1.322 | 21.747 | 0.153 | -1.109 | 22.162 | 0.155 |
| 113 | -1.298 | 21.845 | 0.154 | -1.078 | 22.265 | 0.156 |
| 114 | -1.275 | 21.944 | 0.154 | -1.049 | 22.368 | 0.157 |
| 115 | -1.253 | 22.043 | 0.155 | -1.022 | 22.471 | 0.157 |
| 116 | -1.231 | 22.142 | 0.156 | -0.996 | 22.574 | 0.158 |
| 117 | -1.209 | 22.241 | 0.156 | -0.972 | 22.676 | 0.158 |
| 118 | -1.189 | 22.340 | 0.157 | -0.950 | 22.778 | 0.159 |
| 119 | -1.168 | 22.439 | 0.158 | -0.929 | 22.880 | 0.159 |
| 120 | -1.149 | 22.538 | 0.158 | -0.910 | 22.982 | 0.160 |
| 121 | -1.130 | 22.637 | 0.159 | -0.893 | 23.083 | 0.160 |
| 122 | -1.111 | 22.736 | 0.159 | -0.877 | 23.184 | 0.161 |
| 123 | -1.093 | 22.835 | 0.160 | -0.863 | 23.285 | 0.161 |
| 124 | -1.075 | 22.933 | 0.160 | -0.850 | 23.385 | 0.162 |
| 125 | -1.058 | 23.032 | 0.161 | -0.838 | 23.486 | 0.162 |
| 126 | -1.042 | 23.130 | 0.161 | -0.828 | 23.585 | 0.162 |
| 127 | -1.026 | 23.229 | 0.162 | -0.819 | 23.685 | 0.162 |
| 128 | -1.010 | 23.327 | 0.162 | -0.811 | 23.784 | 0.163 |
| 129 | -0.995 | 23.426 | 0.163 | -0.805 | 23.882 | 0.163 |
| 130 | -0.980 | 23.524 | 0.163 | -0.799 | 23.980 | 0.163 |
| 131 | -0.966 | 23.622 | 0.164 | -0.795 | 24.077 | 0.163 |
| 132 | -0.952 | 23.720 | 0.164 | -0.792 | 24.174 | 0.163 |
| 133 | -0.939 | 23.818 | 0.164 | -0.791 | 24.270 | 0.163 |
| 134 | -0.927 | 23.917 | 0.164 | -0.791 | 24.364 | 0.163 |
| 135 | -0.915 | 24.014 | 0.165 | -0.792 | 24.458 | 0.163 |
| 136 | -0.904 | 24.112 | 0.165 | -0.794 | 24.551 | 0.162 |
| 137 | -0.893 | 24.210 | 0.165 | -0.798 | 24.642 | 0.162 |
| 138 | -0.882 | 24.308 | 0.165 | -0.803 | 24.733 | 0.162 |
| 139 | -0.873 | 24.406 | 0.165 | -0.809 | 24.822 | 0.162 |
| 140 | -0.864 | 24.504 | 0.166 | -0.816 | 24.910 | 0.162 |
| 141 | -0.855 | 24.602 | 0.166 | -0.824 | 24.996 | 0.161 |
| 142 | -0.847 | 24.700 | 0.166 | -0.834 | 25.081 | 0.161 |
| 143 | -0.840 | 24.799 | 0.166 | -0.844 | 25.165 | 0.161 |
| 144 | -0.833 | 24.898 | 0.166 | -0.856 | 25.246 | 0.160 |
| 145 | -0.827 | 24.997 | 0.166 | -0.868 | 25.326 | 0.160 |
| 146 | -0.821 | 25.097 | 0.165 | -0.881 | 25.405 | 0.160 |
| 147 | -0.816 | 25.197 | 0.165 | -0.894 | 25.482 | 0.159 |
| 148 | -0.811 | 25.297 | 0.165 | -0.908 | 25.557 | 0.159 |
| 149 | -0.807 | 25.398 | 0.165 | -0.923 | 25.630 | 0.158 |
| 150 | -0.804 | 25.499 | 0.165 | -0.937 | 25.702 | 0.158 |
| 151 | -0.801 | 25.600 | 0.165 | -0.952 | 25.772 | 0.158 |
| 152 | -0.798 | 25.702 | 0.164 | -0.966 | 25.840 | 0.157 |
| 153 | -0.796 | 25.804 | 0.164 | -0.981 | 25.907 | 0.157 |
| 154 | -0.795 | 25.906 | 0.164 | -0.995 | 25.973 | 0.156 |
| 155 | -0.794 | 26.008 | 0.163 | -1.010 | 26.038 | 0.156 |
| 156 | -0.793 | 26.111 | 0.163 | -1.024 | 26.102 | 0.156 |
| 157 | -0.793 | 26.214 | 0.163 | -1.038 | 26.166 | 0.155 |
| 158 | -0.794 | 26.316 | 0.162 | -1.052 | 26.229 | 0.155 |
| 159 | -0.794 | 26.419 | 0.162 | -1.066 | 26.291 | 0.155 |
| 160 | -0.796 | 26.521 | 0.161 | -1.079 | 26.352 | 0.154 |
| 161 | -0.797 | 26.624 | 0.161 | -1.092 | 26.412 | 0.154 |
| 162 | -0.799 | 26.726 | 0.160 | -1.105 | 26.471 | 0.153 |
| 163 | -0.801 | 26.829 | 0.160 | -1.117 | 26.528 | 0.153 |
| 164 | -0.804 | 26.931 | 0.159 | -1.128 | 26.583 | 0.153 |
| 165 | -0.807 | 27.032 | 0.159 | -1.139 | 26.637 | 0.152 |
| 166 | -0.811 | 27.134 | 0.158 | -1.149 | 26.690 | 0.152 |
| 167 | -0.814 | 27.235 | 0.158 | -1.159 | 26.740 | 0.152 |
| 168 | -0.819 | 27.336 | 0.157 | -1.168 | 26.789 | 0.152 |
| 169 | -0.823 | 27.437 | 0.157 | -1.177 | 26.835 | 0.151 |
| 170 | -0.828 | 27.537 | 0.156 | -1.185 | 26.879 | 0.151 |
| 171 | -0.833 | 27.637 | 0.156 | -1.192 | 26.921 | 0.151 |
| 172 | -0.838 | 27.736 | 0.155 | -1.199 | 26.961 | 0.151 |
| 173 | -0.844 | 27.835 | 0.155 | -1.205 | 26.999 | 0.150 |
| 174 | -0.849 | 27.933 | 0.154 | -1.211 | 27.035 | 0.150 |
| 175 | -0.855 | 28.030 | 0.154 | -1.216 | 27.069 | 0.150 |
| 176 | -0.862 | 28.127 | 0.153 | -1.221 | 27.101 | 0.150 |
| 177 | -0.868 | 28.222 | 0.152 | -1.226 | 27.131 | 0.150 |
| 178 | -0.874 | 28.317 | 0.152 | -1.230 | 27.159 | 0.150 |
| 179 | -0.881 | 28.410 | 0.151 | -1.234 | 27.186 | 0.150 |
| 180 | -0.887 | 28.503 | 0.151 | -1.238 | 27.212 | 0.149 |
| 181 | -0.894 | 28.594 | 0.150 | -1.241 | 27.236 | 0.149 |
| 182 | -0.901 | 28.685 | 0.149 | -1.245 | 27.259 | 0.149 |
| 183 | -0.908 | 28.775 | 0.149 | -1.248 | 27.280 | 0.149 |
| 184 | -0.915 | 28.863 | 0.148 | -1.251 | 27.301 | 0.149 |
| 185 | -0.922 | 28.950 | 0.148 | -1.253 | 27.321 | 0.149 |
| 186 | -0.929 | 29.037 | 0.147 | -1.256 | 27.339 | 0.149 |
| 187 | -0.936 | 29.122 | 0.146 | -1.258 | 27.357 | 0.149 |
| 188 | -0.943 | 29.206 | 0.146 | -1.261 | 27.374 | 0.149 |
| 189 | -0.949 | 29.289 | 0.145 | -1.263 | 27.391 | 0.149 |
| 190 | -0.956 | 29.370 | 0.145 | -1.265 | 27.408 | 0.149 |
| 191 | -0.963 | 29.450 | 0.144 | -1.267 | 27.424 | 0.149 |
| 192 | -0.970 | 29.529 | 0.143 | -1.269 | 27.441 | 0.149 |
| 193 | -0.977 | 29.607 | 0.143 | -1.271 | 27.458 | 0.149 |
| 194 | -0.984 | 29.683 | 0.142 | -1.273 | 27.475 | 0.149 |
| 195 | -0.990 | 29.757 | 0.142 | -1.276 | 27.493 | 0.149 |
| 196 | -0.997 | 29.831 | 0.141 | -1.278 | 27.512 | 0.149 |
| 197 | -1.004 | 29.902 | 0.141 | -1.280 | 27.532 | 0.149 |
| 198 | -1.010 | 29.973 | 0.140 | -1.283 | 27.553 | 0.149 |
| 199 | -1.016 | 30.042 | 0.140 | -1.286 | 27.577 | 0.149 |
| 200 | -1.023 | 30.110 | 0.139 | -1.289 | 27.602 | 0.149 |
| 201 | -1.029 | 30.176 | 0.139 | -1.292 | 27.628 | 0.149 |
| 202 | -1.035 | 30.242 | 0.138 | -1.295 | 27.656 | 0.149 |
| 203 | -1.041 | 30.306 | 0.138 | -1.298 | 27.686 | 0.149 |
| 204 | -1.047 | 30.369 | 0.137 | -1.302 | 27.718 | 0.149 |
| 205 | -1.053 | 30.432 | 0.137 | -1.305 | 27.751 | 0.149 |
| 206 | -1.059 | 30.494 | 0.136 | -1.309 | 27.787 | 0.149 |
| 207 | -1.065 | 30.555 | 0.136 | -1.313 | 27.824 | 0.149 |
| 208 | -1.071 | 30.615 | 0.136 | -1.317 | 27.863 | 0.149 |
| 209 | -1.076 | 30.675 | 0.135 | -1.321 | 27.903 | 0.149 |
| 210 | -1.082 | 30.734 | 0.135 | -1.325 | 27.945 | 0.149 |
| 211 | -1.088 | 30.793 | 0.134 | -1.329 | 27.988 | 0.149 |
| 212 | -1.093 | 30.851 | 0.134 | -1.334 | 28.032 | 0.149 |
| 213 | -1.099 | 30.909 | 0.133 | -1.338 | 28.078 | 0.149 |
| 214 | -1.105 | 30.966 | 0.133 | -1.342 | 28.125 | 0.149 |
| 215 | -1.110 | 31.023 | 0.133 | -1.346 | 28.173 | 0.150 |
| 216 | -1.116 | 31.079 | 0.132 | -1.351 | 28.222 | 0.150 |
| 217 | -1.121 | 31.135 | 0.132 | -1.355 | 28.273 | 0.150 |
| 218 | -1.126 | 31.190 | 0.131 | -1.360 | 28.325 | 0.150 |
| 219 | -1.131 | 31.245 | 0.131 | -1.365 | 28.377 | 0.150 |
| 220 | -1.136 | 31.300 | 0.130 | -1.369 | 28.429 | 0.150 |

TABLE 2-continued

| Age (mos) | Males L | Males M | Males S | Females L | Females M | Females S |
|---|---|---|---|---|---|---|
| 221 | −1.142 | 31.355 | 0.130 | −1.374 | 28.481 | 0.150 |
| 222 | −1.147 | 31.409 | 0.130 | −1.378 | 28.533 | 0.150 | z-score calculation where $L \neq 0$
$z_i = (((x_i/M)^{\wedge} L) - 1)/(LS)$.
z-score calculation where $L = 0$
$z_i = \ln(x_i/M)/S$.

Example 4

This example illustrates z scores obtained using LMS for measurements other than MUAC for children up to 55 weeks of post menstrual age (gestational age plus chronological age). In generating the data detailed in Table 3, it was determined that the circumferences of the middle thigh (MTC), chest (CC), and abdomen (AC), when measured as described above, are strongly correlated with weight. The correlation coefficients are as follows: weight r2: 0.93, 0.95, 0.90 for MTC, CC and AC, respectively; height r2: 0.85, 0.89, 0.91 for MTC, CC and AC, respectively.

TABLE 3

Mid Thigh circumference (males and females combined)

| Post menstrual age (weeks) | L | M | S |
|---|---|---|---|
| 27 | −1.12547 | 7.322662 | 0.104284 |
| 28 | −1.00891 | 7.890045 | 0.104426 |
| 29 | −0.89236 | 8.458449 | 0.104569 |
| 30 | −0.7758 | 9.028895 | 0.104711 |
| 31 | −0.65847 | 9.606316 | 0.104855 |
| 32 | −0.54047 | 10.19141 | 0.104999 |
| 33 | −0.42197 | 10.78314 | 0.105144 |
| 34 | −0.30359 | 11.37527 | 0.105288 |
| 35 | −0.18599 | 11.96189 | 0.105432 |
| 36 | −7.00E−02 | 12.53576 | 0.105574 |
| 37 | 4.39E−02 | 13.09172 | 0.105713 |
| 38 | 0.155975 | 13.6356 | 0.10585 |
| 39 | 0.266923 | 14.17306 | 0.105986 |
| 40 | 0.375951 | 14.69621 | 0.106119 |
| 41 | 0.483568 | 15.20906 | 0.106251 |
| 42 | 0.591414 | 15.72587 | 0.106383 |
| 43 | 0.700559 | 16.25612 | 0.106516 |
| 44 | 0.811265 | 16.80256 | 0.106652 |
| 45 | 0.922443 | 17.35506 | 0.106787 |
| 46 | 1.033073 | 17.90412 | 0.106923 |
| 47 | 1.14246 | 18.44349 | 0.107056 |
| 48 | 1.249745 | 18.96552 | 0.107188 |
| 49 | 1.354107 | 19.46322 | 0.107315 |
| 50 | 1.455709 | 19.93855 | 0.107439 |
| 51 | 1.555527 | 20.39988 | 0.107561 |
| 52 | 1.654644 | 20.85594 | 0.107683 |
| 53 | 1.753637 | 21.31117 | 0.107804 |
| 54 | 1.852676 | 21.76685 | 0.107925 |
| 55 | 1.951738 | 22.22273 | 0.108046 |

TABLE 4

Chest Circumference (males and females combined)

| Post menstrual age (weeks) | L | M | S |
|---|---|---|---|
| 27 | 0.464466 | 19.82165 | 6.84E−02 |
| 28 | 0.444882 | 20.77386 | 6.80E−02 |

TABLE 4-continued

Chest Circumference (males and females combined)

| Post menstrual age (weeks) | L | M | S |
|---|---|---|---|
| 29 | 0.425297 | 21.72951 | 6.75E−02 |
| 30 | 0.405713 | 22.69205 | 0.06711 |
| 31 | 0.385962 | 23.67329 | 6.67E−02 |
| 32 | 0.366071 | 24.67588 | 0.06626 |
| 33 | 0.346031 | 25.70185 | 6.58E−02 |
| 34 | 0.325892 | 26.7451 | 6.54E−02 |
| 35 | 0.30573 | 27.79745 | 0.064967 |
| 36 | 0.285641 | 28.85031 | 6.45E−02 |
| 37 | 0.265763 | 29.89229 | 6.41E−02 |
| 38 | 0.246211 | 30.9202 | 6.37E−02 |
| 39 | 0.227227 | 31.91376 | 6.33E−02 |
| 40 | 0.209038 | 32.85575 | 6.29E−02 |
| 41 | 0.191728 | 33.74672 | 6.25E−02 |
| 42 | 0.175324 | 34.58977 | 6.22E−02 |
| 43 | 0.159873 | 35.3818 | 6.18E−02 |
| 44 | 0.145401 | 36.1197 | 6.15E−02 |
| 45 | 0.131979 | 36.79626 | 6.12E−02 |
| 46 | 0.119594 | 37.41171 | 6.10E−02 |
| 47 | 0.108161 | 37.97224 | 6.07E−02 |
| 48 | 9.76E−02 | 38.4839 | 6.05E−02 |
| 49 | 8.77E−02 | 38.95449 | 6.03E−02 |
| 50 | 7.84E−02 | 39.39504 | 6.01E−02 |
| 51 | 6.95E−02 | 39.81699 | 5.99E−02 |
| 52 | 6.07E−02 | 40.2298 | 5.97E−02 |
| 53 | 5.20E−02 | 40.64092 | 5.95E−02 |
| 54 | 4.32E−02 | 41.05242 | 5.93E−02 |
| 55 | 3.45E−02 | 41.46424 | 5.91E−02 |

TABLE 5

Abdominal Circumference (males and females combined)

| Post menstrual age (weeks) | L | M | S |
|---|---|---|---|
| 27 | 0.411093 | 20.58405 | 7.15E−02 |
| 28 | 0.426755 | 21.55277 | 7.18E−02 |
| 29 | 0.442417 | 22.527 | 7.21E−02 |
| 30 | 0.458079 | 23.51225 | 7.23E−02 |
| 31 | 0.473845 | 24.51841 | 7.26E−02 |
| 32 | 0.489575 | 25.53 | 0.072934 |
| 33 | 0.505089 | 26.52107 | 7.32E−02 |
| 34 | 0.520115 | 27.45283 | 0.073506 |
| 35 | 0.534478 | 28.30728 | 7.38E−02 |
| 36 | 0.548151 | 29.0887 | 7.40E−02 |
| 37 | 0.561281 | 29.81715 | 7.43E−02 |
| 38 | 0.574498 | 30.56576 | 0.074525 |
| 39 | 0.587988 | 31.35169 | 7.48E−02 |
| 40 | 0.60162 | 32.15553 | 7.50E−02 |
| 41 | 0.615375 | 32.97901 | 7.53E−02 |
| 42 | 0.629005 | 33.79831 | 0.075546 |
| 43 | 0.642322 | 34.60039 | 7.58E−02 |
| 44 | 0.655111 | 35.36763 | 7.60E−02 |
| 45 | 0.66717 | 36.08266 | 7.63E−02 |
| 46 | 0.678331 | 36.73132 | 7.65E−02 |
| 47 | 0.688655 | 37.32224 | 7.67E−02 |
| 48 | 0.698164 | 37.85835 | 7.68E−02 |
| 49 | 0.706831 | 38.33796 | 7.70E−02 |
| 50 | 0.714702 | 38.76521 | 0.077151 |
| 51 | 0.721965 | 39.15374 | 7.73E−02 |
| 52 | 0.728902 | 39.52201 | 7.74E−02 |
| 53 | 0.735766 | 39.88597 | 7.75E−02 |
| 54 | 0.742679 | 40.25312 | 7.77E−02 |
| 55 | 0.749624 | 40.6223 | 7.78E−02 |

Example 5

This example illustrates z scores obtained using LMS for MUAC measurements for children up to 55 weeks of post menstrual age (gestational age plus chronological age). Table 6

| Age | L | M | S |
|---|---|---|---|
| 27 | −1.50705 | 5.204456 | 9.60E−02 |
| 28 | −1.36221 | 5.54182 | 9.68E−02 |
| 29 | −1.21738 | 5.8828 | 9.75E−02 |
| 30 | −1.07254 | 6.231014 | 9.82E−02 |
| 31 | −0.92422 | 6.59941 | 9.90E−02 |
| 32 | −0.77259 | 6.994292 | 9.98E−02 |
| 33 | −0.61727 | 7.41864 | 0.100547 |
| 34 | −0.459 | 7.865008 | 0.101345 |
| 35 | −0.29823 | 8.331139 | 0.102254 |
| 36 | −0.13656 | 8.808112 | 0.103234 |
| 37 | 2.34E−02 | 9.283344 | 0.103983 |
| 38 | 0.178288 | 9.744143 | 0.10409 |
| 39 | 0.324063 | 10.16997 | 0.103327 |
| 40 | 0.456342 | 10.53853 | 0.101877 |
| 41 | 0.575261 | 10.85917 | 0.100182 |
| 42 | 0.683784 | 11.14999 | 0.098453 |
| 43 | 0.786568 | 11.43184 | 9.67E−02 |
| 44 | 0.885746 | 11.71175 | 9.50E−02 |
| 45 | 0.980038 | 11.98133 | 9.35E−02 |
| 46 | 1.066813 | 12.2275 | 9.21E−02 |
| 47 | 1.145699 | 12.44839 | 9.08E−02 |
| 48 | 1.216893 | 12.645 | 8.97E−02 |
| 49 | 1.280363 | 12.81768 | 0.088806 |
| 50 | 1.33682 | 12.96927 | 8.80E−02 |
| 51 | 1.38849 | 13.10688 | 8.72E−02 |
| 52 | 1.438082 | 13.23855 | 8.65E−02 |
| 53 | 1.487393 | 13.36943 | 8.58E−02 |
| 54 | 1.536883 | 13.50085 | 8.51E−02 |
| 55 | 1.5865 | 13.63263 | 8.43E−02 |

What is claimed is:

1. An apparatus for estimating the nutritional status of an individual, said apparatus comprising:
   a measurement device configured to measure a circumference of a body part of an individual;
   a first scale that provides a first measurement value when the measurement device is used to measure the circumference of the body part of the individual;
   a plurality of designated ages or age ranges; and
   a plurality of second scales, wherein each of said plurality of second scales is associated with a designated age or age range and provides a plurality of age-specific second standard score values indicating nutritional status ranges at, above, or below a nutritional norm for the designated age or age range,
   wherein said first measurement value corresponds to a second standard score value that estimates the nutritional status of the individual for said designated age or age range when the measurement device is used to measure the circumference of the body part of the individual,
   wherein the measurement device includes a flexible elongate strip, and wherein said designated ages or age ranges, and said first and second scales are each scales of indicia located on said flexible elongate strip, and wherein said first scale of indicia provides said first measurement value when said flexible elongate strip is used to measure the circumference of a body part of an individual, and
   wherein said first measurement is a linear measurement scale, and wherein said second scale of indicia comprises a plurality of rows of elongated bands in alignment with said linear measurement scale, each of said rows corresponding to a designated age or age range indicated on said elongate strip.

2. The apparatus of claim 1, wherein each of said plurality of second scales is derived from circumference measurements of the body part of female individuals.

3. The apparatus of claim 1, wherein each of said plurality of second scales is derived from circumference measurements of the body part of male individuals.

4. The apparatus of claim 1, wherein said first scale includes 1 mm gradations.

5. The apparatus of claim 1, wherein said second scale includes quarter standard, $\frac{1}{10}^{th}$, or $\frac{1}{100}^{th}$ standard score value gradations.

6. The apparatus of claim 1, wherein said indicia on each of said first scale of indicia and said plurality of second scales of indicia are in a form selected from the group consisting of numbers, letters, symbols, colors, and combinations thereof.

7. The apparatus of claim 1, wherein the body part is selected from the group consisting of the middle upper arm, middle thigh, chest, and abdomen.

8. The apparatus of claim 1, wherein the second scale includes z scores obtained from lambda, mu, and sigma values.

9. The apparatus of claim 1, wherein said second standard score values comprise numerical indicia of said nutritional status ranges.

10. The apparatus of claim 9, said second standard score values further comprising color indicia of said nutritional status ranges.

11. An apparatus for estimating the nutritional status of an individual, said apparatus comprising:
    a measurement device configured to measure a circumference of a body part of an individual;
    a plurality of designated ages or age ranges;
    a first scale that provides a first measurement value when said measurement device is used to measure the circumference of the body part of the individual;
    a plurality of second scales, wherein each of said plurality of second scales is associated with a designated age or age range and provides a plurality of age-specific second standard score values indicating ranges of nutritional status at, above, or below a nutritional norm for the designated age or age range;
    a third scale that provides a third measurement value when said measurement device is used to measure the circumference of a body part of an individual;
    a plurality of fourth scales that are each associated with a designated age or age range and provide a plurality of age-specific fourth standard score values indicating ranges of nutritional status at, above, or below a nutritional norm for the designated age or age range;
    wherein said first measurement value corresponds to a second standard score value that estimates the nutritional status of an individual member of a first population group for said designated age or age range when the measurement device is used to measure the circumference of the body part of the individual of the first population group;
    wherein said third measurement value corresponds to a fourth standard score value that estimates the nutritional status of an individual member of a second population group for said designated age or age range when the measurement device is used to measure the circumference of the body part of the individual of the second population group;

wherein the measurement device includes a flexible elongate strip having a front side and a back side, and wherein said first, second, third, and fourth scales are scales of indicia, said front side of said flexible elongate strip having said first scale of indicia and said plurality of second scales of indicia thereon and said back side having said third scale of indicia and said plurality of fourth scales of indicia thereon; and wherein said first measurement is a linear measurement scale, and wherein said second scale of indicia comprises a plurality of rows of elongated bands in alignment with said linear measurement scale, each of said rows corresponding to a designated age or age range indicated on said elongate strip.

12. The apparatus of claim 11, wherein each of said plurality of second scales is derived from circumference measurements of the body part of female individuals.

13. The apparatus of claim 11, wherein each of said plurality of fourth scales is derived from circumference measurements of the body part of male individuals.

14. The apparatus of claim 11, wherein:
   a. each of said plurality of second scales provides a plurality of age-specific second standard score values for a first group of designated ages or age ranges; and
   b. each of said plurality of fourth scales provides a plurality of age-specific fourth standard score values for a second group of designated ages or age ranges.

15. The apparatus of claim 11, wherein said first scale includes 1 mm gradations and said third scale includes 1 mm gradations.

16. The apparatus of claim 11, wherein said second scale and said fourth scale each include quarter, $1/10^{th}$, or $1/100^{th}$ standard score value gradations.

17. The apparatus of claim 11, wherein said indicia on each said scale of indicia and each said plurality of scales of indicia are in a form selected from the group consisting of numbers, letters, symbols, colors, and combinations thereof.

18. The apparatus of claim 11, wherein the body part is selected from the group consisting of the middle upper arm, middle thigh, chest, and abdomen.

19. The apparatus of claim 11, wherein the second scale includes z scores obtained from lambda, mu, and sigma values.

* * * * *